United States Patent
Kim et al.

(10) Patent No.: US 10,175,325 B2
(45) Date of Patent: Jan. 8, 2019

(54) SYSTEM, METHOD, AND COMPUTER-ACCESSIBLE MEDIUM FOR DETERMINING AT LEAST ONE CHARACTERISTIC OF AT LEAST ONE TISSUE OR AT LEAST ONE MRI MEASUREMENT CONDITION OF THE AT LEAST ONE TISSUE USING ACTIVE CONTRAST ENCODING MAGNETIC RESONANCE IMAGING PROCEDURE(S)

(71) Applicant: New York University, New York, NY (US)

(72) Inventors: Sungheon Gene Kim, Millburn, NJ (US); Jin Zhang, Union City, NJ (US)

(73) Assignee: New York University, New York, NY (US)

( * ) Notice: Subject to any disclaimer, the term of this patent is extended or adjusted under 35 U.S.C. 154(b) by 582 days.

(21) Appl. No.: 14/696,951

(22) Filed: Apr. 27, 2015

(65) Prior Publication Data

US 2015/0309141 A1    Oct. 29, 2015

Related U.S. Application Data

(60) Provisional application No. 61/984,384, filed on Apr. 25, 2014.

(51) Int. Cl.
*A61B 5/055* (2006.01)
*G01R 33/56* (2006.01)
(Continued)

(52) U.S. Cl.
CPC .......... *G01R 33/5601* (2013.01); *A61B 5/055* (2013.01); *G01R 33/561* (2013.01);
(Continued)

(58) Field of Classification Search
CPC .............. G01R 33/5601; G01R 33/561; G01R 33/5659; G01R 33/56366;
(Continued)

(56) References Cited

U.S. PATENT DOCUMENTS

| | | | |
|---|---|---|---|
| 6,198,960 B1 * | 3/2001 | Fain | G01R 33/563 324/306 |
| 9,013,182 B2 * | 4/2015 | Jena | G01R 33/50 324/306 |

(Continued)

OTHER PUBLICATIONS

Liberman et al. "T1 Mapping Using Variable Flip Angle SPGR Data With Flip Angle Correction" J MRI 40 (2014), 171-180.*
(Continued)

*Primary Examiner* — Angela M Hoffa
(74) *Attorney, Agent, or Firm* — Hunton Andrews Kurth LLP

(57) ABSTRACT

In another exemplary embodiment of the present disclosure is an exemplary system, method and computer-accessible for determining a characteristic(s) of a tissue(s), that can include, for example, receiving magnetic resonance imaging information regarding the tissue(s) including a time-intensity curve(s) of the tissue(s) based on a contrast agent(s) concentration, actively encoding a part of the time-intensity curve(s) with a magnetic resonance relaxation property(s) of the tissue(s) by varying a magnetic resonance imaging scan parameter(s) to generate encoded data during magnetic resonance data acquisition, and determining the tissue characteristic(s) based on the encoded data.

17 Claims, 14 Drawing Sheets

(51) Int. Cl.
G01R 33/561 (2006.01)
G01R 33/563 (2006.01)
G01R 33/24 (2006.01)
G01R 33/565 (2006.01)

(52) U.S. Cl.
CPC ... *G01R 33/5659* (2013.01); *G01R 33/56366* (2013.01); *G01R 33/24* (2013.01); *G01R 33/243* (2013.01); *G01R 33/246* (2013.01); *G01R 33/56563* (2013.01)

(58) Field of Classification Search
CPC ............ G01R 33/56563; G01R 33/243; G01R 33/24; G01R 33/246; A61B 5/055
See application file for complete search history.

(56) References Cited

U.S. PATENT DOCUMENTS

2013/0154638 A1\* 6/2013 Jena ................. G01R 33/50 324/309
2017/0172453 A1\* 6/2017 Madore ............... A61B 5/0555

OTHER PUBLICATIONS

Yuan et al. "Quantitative evaluation of dual-flip-angle T1 mapping on DCE-MRI kinetic parameter estimation in head and neck." Quant Imaging Med Surg 2(4) (2012), 245-253.\*
Dickie et al. "Improved Accuracy and Precision of Tracer Kinetic Parameters by Joint Fitting to Variable Flip Ange and Dynamic Contrast Enhanced MRI Data." MR Med 76 (2016), 1270-1281.\*
Khalifa et al. "Models and methods for analyzing DCE-MRI: A Review." Med Phys 41:12 (Dec. 2014), 32 pages.\*
Hurley et al. "Simultaneous Variable Flip Angle-Actual Flip Angle Imaging Method for Improved Accuracy and Precision of Three-dimensional T1 and B1 Measurements." MR Med 68 (2012), 54-64.\*
Cheng et al. "Rapid High-Resolution T1 Mapping by Variable Flip Angles: Accurate and Precise Measurements in the Presence of Radiofrequency Field Inhomogeneity." MR Medicine 55 (2006), 566-574.\*
Lag, Ries et al., "Cancer Survival Among Adults: U.S. SEER Program, 1988-2001 Patient and Tumor Characteristics," National Cancer Institute, SEER Program, NIH Pub No. 07-6215, pp. 101-110, 2007.
Parker, Geoffrey J.M. et al., "Accurate Multislice Gradient Echo T1 Measurement in the Presence of Non-Ideal RF Pulse Shape and RF Field Nonuniformity," Magnetic Resonance in Medicine, vol. 45, pp. 838-845, 2001.
Parker, Geoff J.M. et al., "Experimentally-Derived Functional Form for a Population-Averaged High-Temporal-Resolution Arterial input Function for Dynamic Contrast-Enhanced MRI," Magnetic Resonance in Medicine, vol. 56, pp. 993-1000, 2006.
Nelder, J.A. et al., "A Simplex Method for Function Minimization," Comput J., vol. 7, No. 4, pp. 308-313, 1965.
Nehrke, Kay, "On the Steady-State Properties of Actual Flip Angle Imaging (AFI)," Magnetic Resonance in Medicine, vol. 61, pp. 84-92, 2009.
Naish, Josephine H. et al., "Modeling of Contrast Agent Kinetics in the Lung using T1-Weighted Dynamic Contrast-Enhanced MRI," Magnetic Resonance in Medicine, vol. 61, pp. 1507-1514, 2009.
Mustafi, Devkumar et al., "High-Resolution Magnetic Resonance Colonography and Dynamic Contrast-Enhanced Magnetic Resonance Imaging in a Murine Model of Colitis," Magn. Reson. Med., vol. 63, No. 4, pp. 922-929, Apr. 2010.
Morrell, Glen R. et al., "A Phase-Sensitive Method of Flip Angle Mapping," Magnetic Resonance in Medicine, vol. 60, pp. 889-894, 2008.
Ma, Dan et al., "Magnetic Resonance Fingerprinting," Nature, vol. 495, pp. 187-192, Mar. 14, 2013.
Look, D.C. et al., "Time Saving in Measurement of NMR and EPR Relaxation Times," The Review of Scientific Instruments, vol. 41, No. 2, p. 250-251, Feb. 1970.
Liberman, Gilad et al., "T1 Mapping Using Variable Flip Angle SPGR Data with Flip Angle Correction," Journal of Magnetic Resonance Imaging, vol. 40, pp. 171-180, 2014.
Kovar, David A. et al., "A New Method for Imaging Perfusion and Contrast Extraction Fraction: Input Functions Derived from Reference Tissues," J. Magn Reson Imaging, vol. 8, No. 5, pp. 1126-1134, 1998.
Kim, S. et al., "Prediction of Response to Chemoradiation Therapy in Squamous Cell Carcinomas of the Head and Neck Using Dynamic Contrast-Enhanced MR Imaging," AJNR, vol. 31, No. 2, 262-268, 2010.
Kim, Sungheon et al., "Transcytolemmal Water Exchange in Pharmacokinetic Analysis of Dynamic Contrast-Enhanced MRI Data in Squamous Cell Carcinoma of the Head and Neck," Journal of Magnetic Resonance Imaging, vol. 26, pp. 1607-1617, 2007.
Jemal, Shmedin et al., "Cancer Statistics, 2009," CA Cancer J. Clin, vol. 59, No. 4, pp. 225-249, Jul./Aug. 2009.
Insko, E.K. et al., "Mapping of the Radiofrequency Field," Journal of Magnetic Resonance, Series A, vol. 103, pp. 82-85, 1993.
Ingrisch, Michael et al., "Quantification of Perfusion and Permeability in Multiple Sclerosis," Investigative Radiology, vol. 47, No. 4, pp. 252-258, Apr. 2012.
Huang, Wei et al., "The Magnetic Resonance Shutter Speed Discriminates Vascular Properties of Malignant and Benign Breast Tumors in Vivo," PNAS, vol. 105, No. 46, pp. 17943-17948, Nov. 18, 2005.
Hodgdon, R. J. et al., "MRI of Rheumatoid Arthritis—Image Quantitation for the Assessment of Disease Activity, Progression and Response to Therapy," Rheumatology, vol. 47, pp. 13-21, Nov. 2007.
Florie, Jasper et al., "Dynamic Contrast-Enhanced MRI of the Bowel Wall for Assessment of Disease Activity in Crohn's Disease," American Journal of Roentgenology, vol. 186, No. 5, pp. 1384-1392, 2006.
Dowell, Nicholas G, et al., "Fast, Accurate, and Precise Mapping of the RF Field in Vivo using the 180 Signal Null," Magnetic Resonance in Medicine, vol. 58, pp. 622-630, 2007.
Deoni, Sean C.L. et al., "Rapid Combined T1 and T2 Mapping using Gradient Recalled Acquisition in the Steady State," Magnetic Resonance in Medicine, vol. 49, pp. 515-526, 2003.
Deoni, Sean C.L. "Correction of Main and Transmit Magnetic Field (B0 and B1) Inhomogeneity Effects in Multicomponent-Driven Equilibrium Single-Pulse Observation of T1 and T2," Magn Reson Med, vol. 65, No. 4, pp. 1021-1035, Apr. 2011.
Deoni, Sean C.L. "High-Resolution T1 Mapping of the Brain at 3T with Driven Equilibrium Single Pulse Observation of T1 with High-Speed Incorporation of RF Field Inhomogeneities (DESPOT1-HIFI)," Journal of Magnetic Resonance Imaging, vol. 26, pp. 1106-1111, 2007.
De Lussanet, Quido G. et al., "Dynamic Contrast-Enhanced MRI of Muscle Perfusion Combined with MR Angiography of Collateral Artery Growth in a Femoral Artery Ligation Model," NMR in Biomedicine, vol. 20, pp. 717-725, 2007.
Cunningham, Charles H. et al., "Saturated Double-Angle Method for Rapid B1+ Mapping," Magnetic Resonance in Medicine, vol. 55, pp. 1326-1333, 2006.
Choyke, Peter L. et al., "Functional Tumor Imaging with Dynamic Contrast-Enhanced Magnetic Resonance Imaging," Journal of Magnetic Resonance Imaging, vol. 17, pp. 509-520, 2003.
Buckley, David L. et al., "Cellular-Interstitial Water Exchange and its Effect on the Determination of Contrast Agent Concentration in Vivo: Dynamic Contrast-Enhanced MRI of Human Internal Obturator Muscle," Magnetic Resonance in Medicine, vol. 60, pp. 1011-1019, 2008.
Buckley, David L., "Uncertainty in the Analysis of Tracer Kinetics Using Dynamic Contrast-Enhanced T1-Weighted MRI," Magnetic Resonance in Medicine, vol. 47, pp. 601-606, 2002.

(56) References Cited

OTHER PUBLICATIONS

Brookes, Jason A. et al., "Accuracy of T1 Measurement in Dynamic Contrast-Enhanced Breast MRI Using Two- and Three-Dimensional Variable Flip Angle Fast Low-Angle Shot," Journal of Magnetic Resonance Imaging, vol. 9, pp. 163-171, 1999.

Bloch, F. et al., "Magnetic Resonance for Nonrotating Fields," Physical Review, vol. 57, pp. 522-527, Mar. 15, 1940.

Balezeau, Fabien et al., Mapping of Low Flip Angles in Magnetic Resonance, Physics in Medicine and Biology, vol. 56, No. 20, pp. 6635-6647, 2011.

Abramson, Richard G. et al., "Early Assessment of Breast Cancer Response to Neoadjuvant Chemotherapy of Semi-Quantitative Analysis of High-Temporal Resolution DCE-MRI: Preliminary Results," Magn Reson Imaging, vol. 31, No. 9, pp. 1457-1464, Nov. 2013.

Zhang, Jin et al., "Uncertainty in MR Tracer Kinetic Parameters and Water Exchange Rates Estimated from T1-Weighted Dynamic Contrast Enhanced MRI," Magnetic Resonance in Medicine, vol. 72, pp. 534-545, 2014.

Zhang, Jin et al., "Estimation of Reference Tissue based Arterial input Function using Neural Network," Proc. intl. Soc. Mag. Reson, Med. vol. 20, p. 1971, 2012.

Yarnykh, Vasily L. et al., "Optimal Radiofrequency and Gradient Spoiling for Improved Accuracy of T1 and B1 Measurements Using Fast Steady-State Techniques," Magnetic Resonance in Medicine, vol. 63, pp. 1610-1626, 2010.

Warner, Ellen et al., "Systematic Review: Using Magnetic Resonance Imaging to Screen Women at High Risk for Breast Cancer," Annals of Internal Medicine, vol. 148, No. 9, pp. 671-679, 2008.

Wang, Jinghua et al., "Measurement and Correction of Transmitter and Receiver Induced Nonuniformities in Vivo," Magnetic Resonance in Medicine, vol. 53, pp. 408-417, 2005.

Wang, Jinghua et al., "T1 Measurements Incorporation Flip Angle Calibration and Correction in Vivo," Journal of Magnetic Resonance, vol. 182, pp. 283-292, 2006.

Wang, Dingxin et al., "Rapid 3D Radiofrequency Field Mapping Using Catalyzed Double-Angle Method," NMR Biomed, vol. 22, No. 8, pp. 882-890, Oct. 2009.

Voigt, Tobias et al., "T1 Corrected B1 Mapping using Multi-TR Gradient Echo Sequences," Magnetic Resonance in Medicine, vol. 64, pp. 725-733, 2010.

Tofts, Paul S. et al., "Estimating Kinetic Parameters from Dynamic Contrast-Enhanced T1-Weighted MRI of a Diffusable Tracer: Standardized Quantities and Symbols," Journal of Magnetic Resonance Imaging, vol. 10, 223-232, 1999.

Sung, Kyunghyun et al., "Transmit B1 Field Inhomogeneity and T1 Estimation Errors in Breast DCE-MRI at 3 Testa," Journal of Magnetic Resonance Imaging, vol. 38, pp. 454-459, 2013.

Stollberger, Rudolf et al., "Imaging of the Active B1 Field in Vivo," MRM, vol. 35, pp. 246-251, 1996.

Sled, John G. et al., "Correction for B1 and B0 Variations in Quantitative T2 Measurements Using MRI," Magnetic Resonance in Medicine, vol. 43, pp. 589-593, 2000.

Scheffler, Klaus et al., "T1 Quantification with Inversion Recovery TrueFISP," Magnetic Resonance in Medicine, vol. 45, pp. 720-723, 2001.

Samson, Rebecca S. et al., "A Simple Correction for B1 Field Errors in Magnetization Transfer Ratio Measurements," Magnetic Resonance Imaging, vol. 24, pp. 255-263, 2006.

Samei, Ehsan et al., Digital Mammography: Effects of Reduced Radiation Dose on Diagnostic Performance, Radiology, vol. 243, No. 2, pp. 396-404, May 2007.

Sacolick, Laura I. et al., "B1 Mapping by Bloch-Siegert Shift," Magn Reson Med, vol. 63, No. 5, pp. 1315-1322, May 2010.

\* cited by examiner

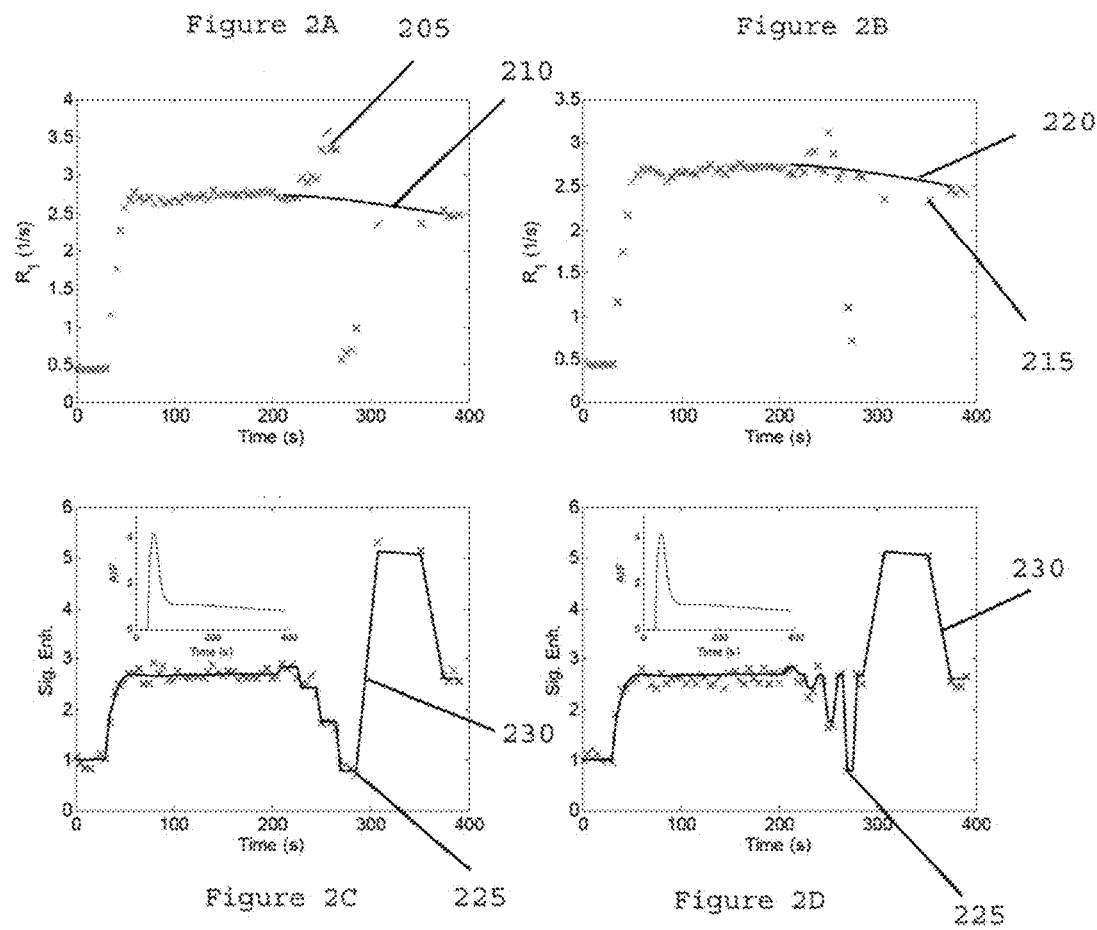

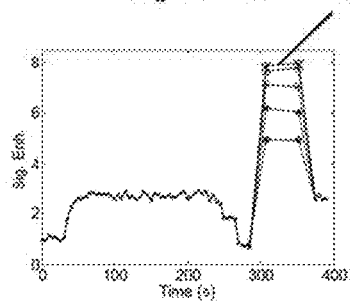
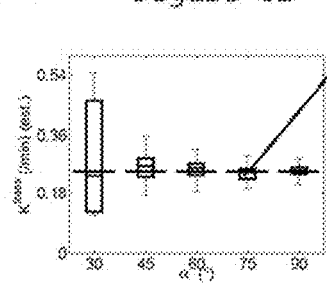
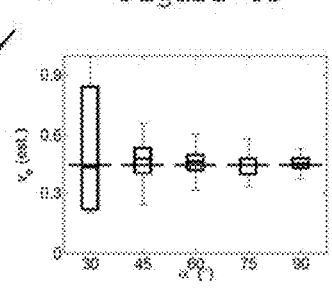
Figure 4A    405        Figure 4B    410        Figure 4C
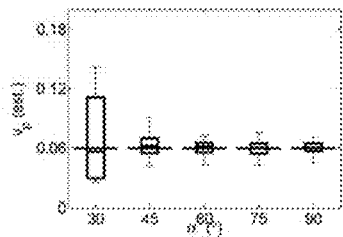
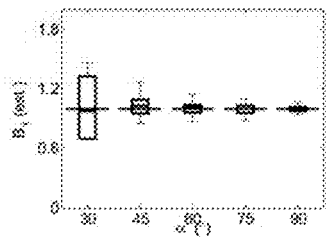
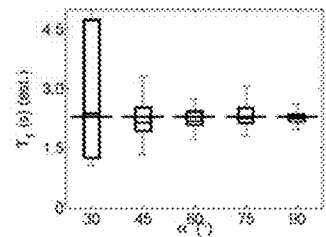
Figure 4D                Figure 4E                Figure 4F

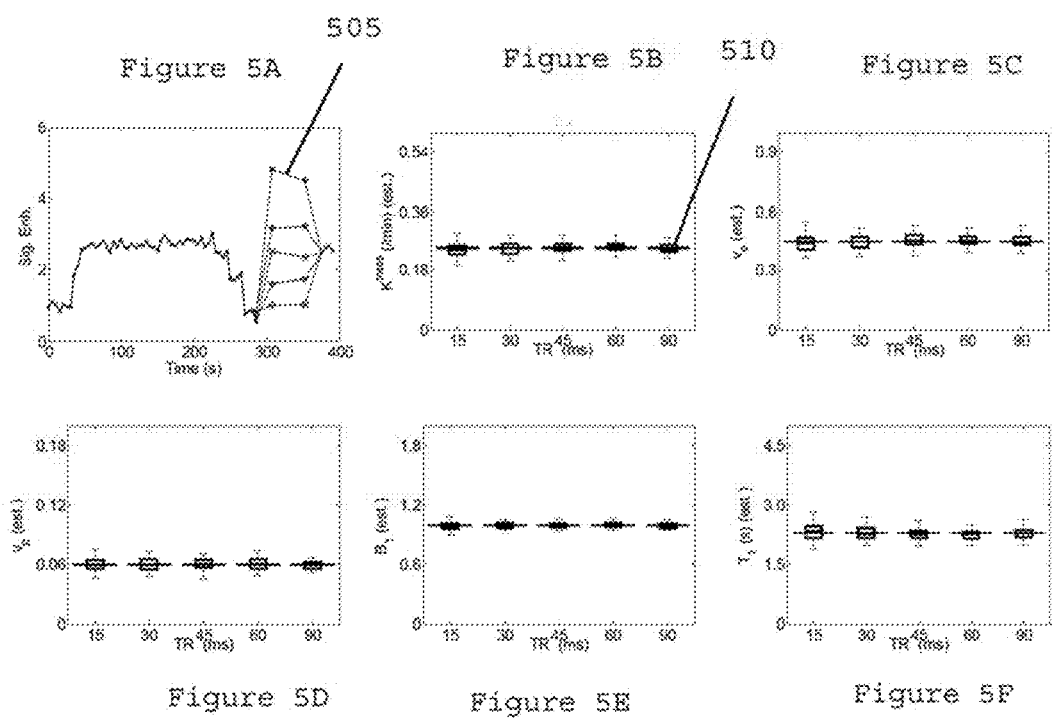

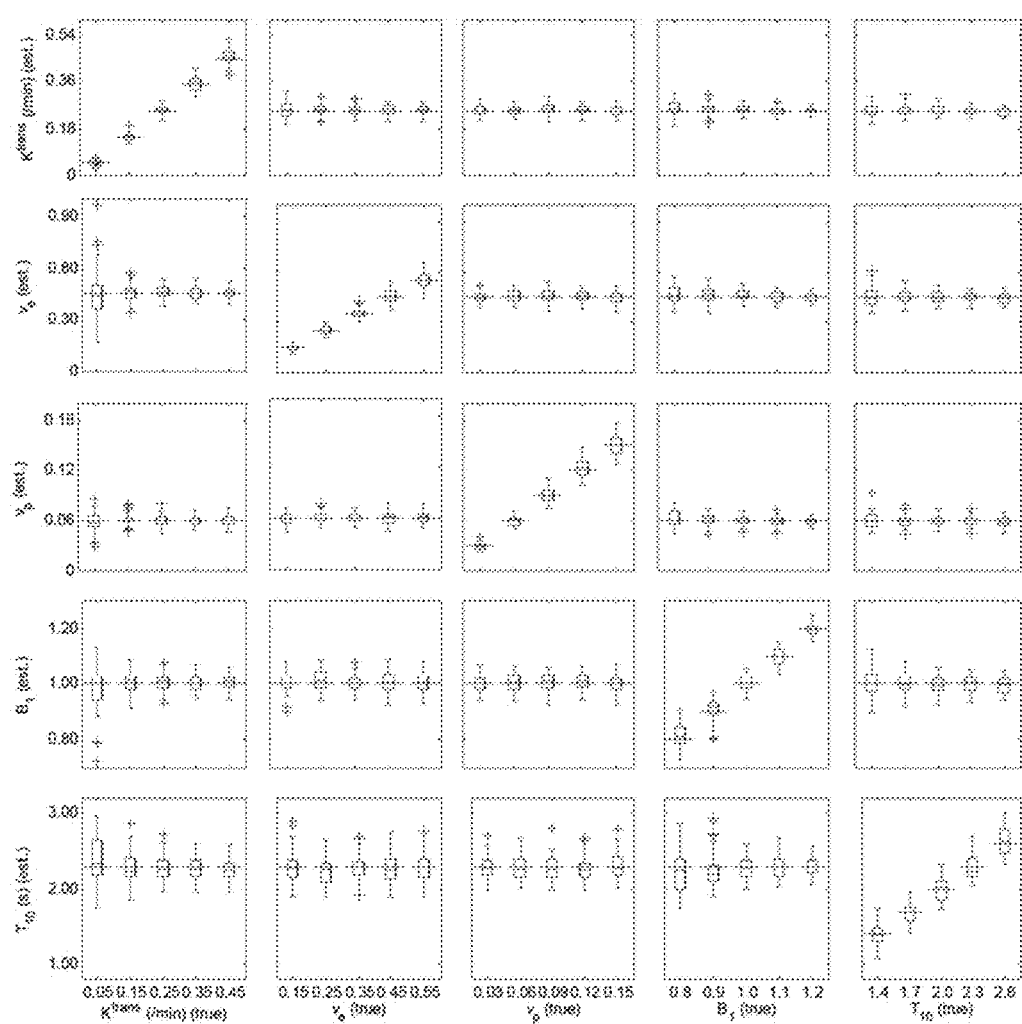

Figure 6K
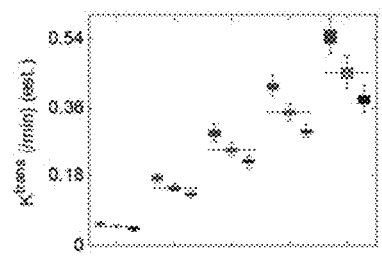
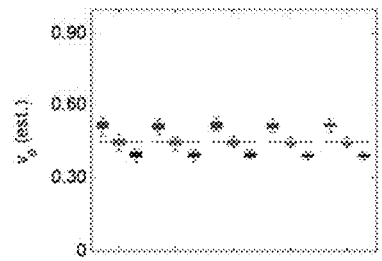
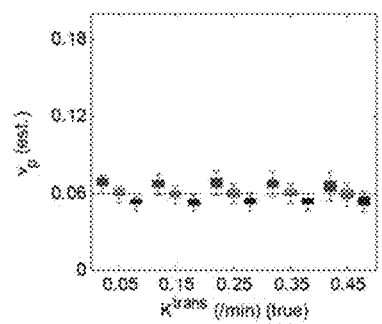
Figure 6L
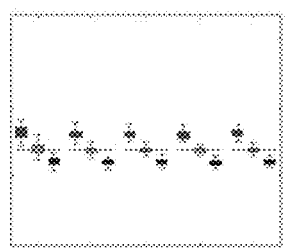
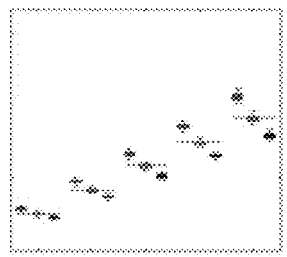
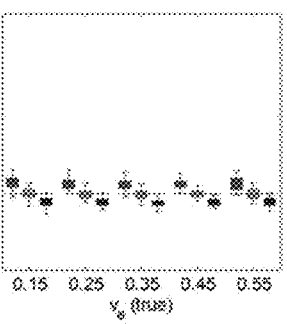
Figure 6M
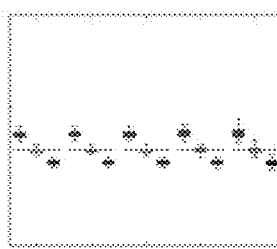
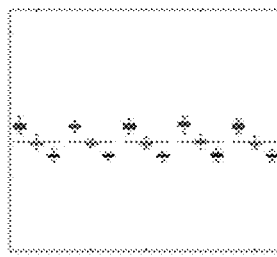
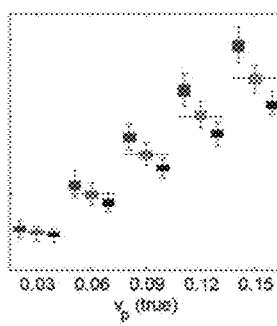

Figure 8A
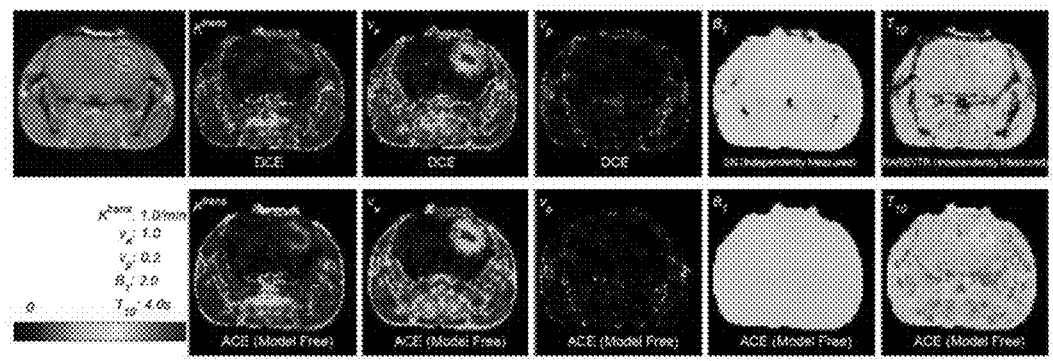
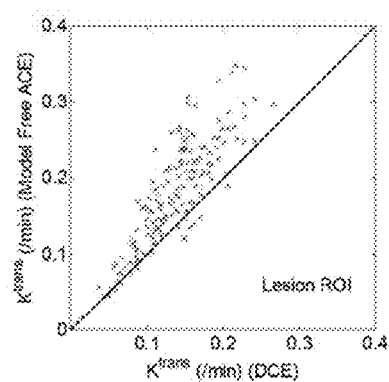
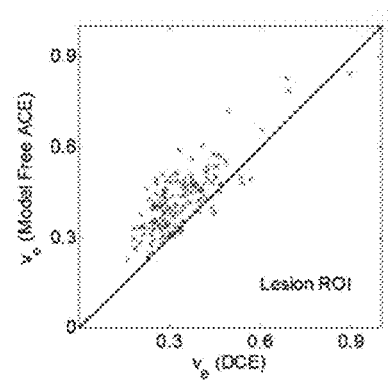
Figure 8B
Figure 8C

SYSTEM, METHOD, AND COMPUTER-ACCESSIBLE MEDIUM FOR DETERMINING AT LEAST ONE CHARACTERISTIC OF AT LEAST ONE TISSUE OR AT LEAST ONE MRI MEASUREMENT CONDITION OF THE AT LEAST ONE TISSUE USING ACTIVE CONTRAST ENCODING MAGNETIC RESONANCE IMAGING PROCEDURE(S)

CROSS-REFERENCE TO RELATED APPLICATION(S)

This application relates to and claims priority from U.S. Patent Application No. 61/984,384, filed on Apr. 25, 2014, the entire disclosure of which is incorporated herein by reference.

STATEMENT REGARDING FEDERALLY SPONSORED RESEARCH

This invention was made with government support under Grant No R01CA160620 awarded by the National Institute of Health. The government has certain rights in the invention.

FIELD OF THE DISCLOSURE

The present disclosure relates generally to magnetic resonance imaging ("MRI"), and more specifically, to exemplary embodiments of systems, methods, and computer-accessible mediums for determining at least one characteristic of at least one tissue or at least one MRI measurement condition of the at least one tissue, by measuring, for example, pharmacokinetic model parameters, pre-contrast magnetic resonance ("MR") relaxation properties (e.g., $T_{10}$ and $T_{20}^*$) and MR measurement conditions (e.g. $B_1$ and $B_0$) using Active Contrast Encoding ("ACE") MRI.

BACKGROUND INFORMATION $T_1$-weighted dynamic contrast enhanced magnetic resonance imaging ("DCE-MRI") can be an important procedure for diagnosis, and for assessing treatment response of cancer (see, e.g., References 1-4), as well as for various inflammatory diseases, such as multiple sclerosis (see, e.g., Reference 5), rheumatoid arthritis (see, e.g., Reference 6), and inflammatory bowel diseases. (See, e.g., References 7 and 8). Time-intensity curves of DCE-MRI can contain rich information about the tissue microcirculation environment, and can be analyzed using contrast kinetic models to estimate physiologically relevant parameters, such as a transfer constant (e.g., $K^{trans}$), plasma volume fraction (e.g., $v_p$), and extravascular extracellular space volume fraction (e.g., $v_e$). (See, e.g., References 9 and 10). However, quantitative analysis of DCE-MRI data remains challenging, particularly due to the need to separately measure the pre-contrast longitudinal relaxation time constant (e.g., $T_{10}$) of the tissue (see, e.g., Reference 9) and actual flip-angles ("FA") achieved for $T_1$ measurement and the dynamic scan. (See, e.g., References 11-13).

The degree of contrast enhancement in a tissue can vary depending on the $T_{10}$ of the tissue, such that analyses of DCE-MRI data based on time-intensity curves without taking into account the $T_{10}$ variability in lesions can result in a limited diagnostic accuracy. (See, e.g., Reference 14). For a more robust quantitative analysis, DCE-MRI time-intensity curves can be converted to contrast agent concentration curves. Such signal-to-concentration conversion process can utilize $T_{10}$ values, which can be measured using various methods, such as inversion recovery (see, e.g., Reference 15 and 16) and variable flip angle methods (see, e.g., Reference 17), but at the cost of extra scan time. In addition, accurate $T_1$ mapping can typically utilize correction for the inhomogeneous radiofrequency ("RF") transmit field (e.g., $B_1$). (See, e.g., References 11 and 18-20). $B_1$ field maps can also be used to correct for the $B_1$ inhomogeneity effect in the $T_1$-weighted DCE-MRI data itself. Various $B_1$ mapping methods have been developed based on either magnitude images (see, e.g., References 21-23) or phase images (see, e.g., References 24-26) which can be made sensitive to the B1 field. Most $B_1$ mapping methods utilize either a long repetition time ("TR") to minimize the tissue $T_1$ effect, or an extra measurement of $B_0$ field to minimize the off-resonance effect, which can lead to a further increase of the scan time. Furthermore, there can be other factors that can also affect the actual FA, such as slice profile (see, e.g., Reference 27) and RF amplifier nonlinearity. (See, e.g., Reference 28). The scan time needed for these additional measurements of $T_{10}$ and FA correction factor (f) can often be similar to, or longer than, the actual DCE-MRI scan itself (See, e.g., References 11 and 29). Given a limited scan time available in most clinical scans, it may not be trivial to conduct a quantitative DCE-MRI experiment with appropriate $T_{10}$ and f measurements. Thus, in order to utilize the full potential of DCE-MRI as a clinical and research tool, it can be beneficial to improve the means to accurately measure and/or correct for $T_{10}$, and other factors affecting FA, without substantially increasing the total scan time.

Fast $B_1$ mapping has been evaluated for many quantitative MRI measurements, including DCE-MRI, as $B_1$ non-uniformity can be one of the main causes of difference between the nominal FA and actual FA. $B_1$ mapping can be performed using either the magnitude or phase of magnetic resonance ("MR") images that can reflect the $B_1$ field strength. There are several $B_1$ mapping techniques based on the magnitude images, such as finding the signal null at a FA of 180° (see, e.g., Reference 23), or calculation of the signal ratio from images with two FAs. (See, e.g., References 21 and 22). Since the image magnitude can depend on $T_1$ of tissue and TR, the magnitude-based methods typically utilize a long TR (e.g., >about $5T_1$) to eliminate the $T_1$ dependence (see, e.g., Reference 21), which can lead to a long scan time. In order to reduce the scan time, fast imaging methods with extended echo-train-length (see, e.g., References 38 and 39), or echo-planar imaging (see, e.g., References 40 and 41), have been used, in addition to employing a means to minimize the effect of not-fully recovered longitudinal magnetization by playing out special RF pulses at the end of the sequence. (See, e.g., References 41 and 42). The phase-based $B_1$ mapping methods use either composite excitation pulse (see, e.g., Reference 24) or an excitation pulse followed by an off-resonance Bloch-Siegert Shift pulse (see, e.g., References 25 and 26), in order to sensitize the phase of the images to the $B_1$ field strength. One of the challenging issues with the phase-based methods can be the influence from the $B_0$ inhomogeneity that can bring a need for additional $B_0$ field mapping at the cost of additional scan time, or careful advanced design of RF pulse. In the case of the Bloch-Siegert Shift method, RF power deposition in the tissue can be another constraint as the measurement accuracy improves with the Bloch-Siegert Shift pulse power. Thus, while these recent developments offer a number of different ways to measure $B_1$ field map, acquiring $B_1$ map during clinical scans still remains technically challenging and an extra burden of scan time and warrants further development.

Thus, it may be beneficial to provide exemplary system, method and computer-accessible medium that can be used to measure both f and $T_{10}$ values, along with kinetic model parameters from dynamic scan data, without having to run additional scans for separate measurement of f and $T_{10}$, and which can address and/or overcome at least some of the deficiencies described herein above.

SUMMARY OF EXEMPLARY EMBODIMENTS

An exemplary system, method and computer-accessible medium for generating an image of a tissue(s) can be provided, which can include, for example, receiving magnetic resonance imaging information regarding the tissue(s) including an intensity(s) of a signal(s) provided from the tissue(s), actively encoding the signal intensity(s) with a flip angle(s) and a repetition time(s) of the pulse sequence (s), and generating the image of the tissue(s) based on the encoded signal intensity(s). A flip angle correction factor(s), and a $T_{10}$ value(s), can be embedded in the magnetic resonance information. The flip angle correction factor(s) can be based on a (i) $B_1$ field inhomogeneity, (ii) a radio frequency pulse profile, (iii) a nonlinearity of a radio frequency amplifier, (iv) properties of the tissue(s), and/or (v) imperfect spoiling in steady-state imaging.

In some exemplary embodiments of the present disclosure, the flip angle(s) can be scaled based on the flip angle correction factor(s) and the contrast kinetic parameters, such as $K^{trans}$, $v^p$ and $v_e$, and can be estimated based on the corrected flip angles and $T_{10}$ value.

The exemplary encoding procedure can be made to estimate other parameters, such as proton density, magnetic field ("$B_0$") and transverse relaxation time ($T_2^*$), based on active encoding of the signal intensity with flip angles, repetition times, and echo times of the pulse sequence.

The encoding procedure can be made to estimate proton densities, $T_{10}$ and $T_2^*$ values of multiple tissue components, such as water and fat, within an imaging voxel.

The encoding procedure can be made in any part during acquisition of DCE-MRI. An exemplary encoding procedure can be based on a slow-varying wash-out portion of a dynamic contrast enhanced magnetic resonance imaging scan. The wash-out portion can be approximated using a contrast agent kinetic model, or as a linear line(s) that can connect a start and an end of an encoding duration with a baseline flip angle and a baseline repetition time. The tissue(s) can be any tissue with capillaries that allow extravasation of contrast agents.

In another exemplary embodiment of the present disclosure is an exemplary system, method and computer-accessible for determining a characteristic(s) of a tissue(s), that can include, for example, generating MRI information by encoding a portion(s) of a time-intensity curve(s) associated with the tissue(s), which can be based on a contrast agent concentration(s), with (i) a magnetic resonance (MR) relaxation property of the tissue(s) and (ii) a MR measurement condition(s), by varying a MRI scan parameter(s), and determining the tissue characteristic(s) based on the MRI information.

In some exemplary embodiments of the present disclosure the magnetic resonance relaxation property(s) can include a $T_1$ value(s) or a $T_2$ value(s). The magnetic resonance relaxation property(s) can include a $T_{10}$ value(s), which can be an estimation of a pre-contrast injection longitudinal relaxation time of the tissue(s). The magnetic resonance relaxation property(s) can include a factor(s) that can estimate a proton density of the tissue(s). The magnetic resonance measurement condition (s) can include a flip angle correction factor(s), which can be based on a radio frequency transmit field $B_1$ inhomogeneity, a radio frequency pulse profile, a nonlinearity of a radio frequency amplifier, properties of the tissue(s), or imperfect spoiling in steady-state imaging.

In some exemplary embodiments of the present disclosure, the magnetic resonance imaging scan parameter(s) can include a flip angle(s) or a repetition time. The flip angle(s) can be scaled based on a flip angle correction factor(s). The active encoding procedure can be based on a portion of a dynamic contrast enhanced-magnetic resonance imaging scan. The portion of the dynamic contrast enhanced-magnetic resonance imaging scan can be approximated as a line(s) (e.g., a linear line), and the line(s), a set of line segments and/or a contrast kinetic model can connect a start and an end of a wash-out phase of the wash-out portion with a baseline flip angle and a baseline repetition time. Alternatively, the portion of the dynamic contrast enhanced-magnetic resonance imaging scan can be approximated using a contrast kinetic model(s). The magnetic resonance relaxation property(s) or the magnetic resonance imaging measurement condition(s) can be approximated based on the portion of the dynamic contrast enhanced-magnetic resonance imaging scan. The tissue characteristic(s) can include a tissue vascular micro-environmental property(s).

In some exemplary embodiment of the present disclosure, the actively encoded portion can be decoded based on a property(s) of a time-contrast agent concentration curve(s). The time-contrast agent concentration curve(s) can be continuous during the encoding.

In certain exemplary embodiments of the present disclosure, the magnetic resonance imaging information can include a dynamic contrast-enhanced curve(s), which can include a slow-varying, wash-out portion, of the dynamic contrast-enhances magnetic resonance imaging curve. A washout portion of the time-intensity curve(s) can be approximated as a continuous curve using either a linear line(s) or a contrast kinetic model, and the tissue characteristic(s) or the magnetic resonance imaging measurement condition(s) can be determined based on the approximated continuous line. The approximated line(s) can connect a beginning and an end of a washout phase having a baseline flip angle and a baseline repetition time. One or more image(s) of the tissue can be generated based on the information.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which:

FIGS. 2A-2D are exemplary graphs illustrating exemplary contrast encoding methods according to an exemplary embodiment of the present disclosure;

FIG. 4A-4F are exemplary graphs illustrating the effect of a flip angle on parameter uncertainty in the exemplary ACE-MRI according to an exemplary embodiment of the present disclosure;

FIGS. 5A-5F are exemplary graphs illustrating the effect of TR of a large flip angle on parameter uncertainty in the exemplary ACE-MRI according to an exemplary embodiment of the present disclosure;

FIGS. 6A-6E are exemplary graphs illustrating the accuracy and precision of parameter estimation in the exemplary ACE-MRI according to an exemplary embodiment of the present disclosure;

FIGS. 6F-6J are exemplary graphs illustrating the coefficient of variation of the exemplary ACE-MRI depending on changes in $K^{trans}$ according to an exemplary embodiment of the present disclosure;

FIGS. 6K-6M are exemplary graphs illustrating the accuracy and precision of contrast kinetic parameters estimated from DCE-MRI on the uncertainty of $T_1$ measurement;

FIG. 8A is a set of exemplary images of in-vivo data processing using an exemplary model-free procedure according to an exemplary embodiment of the present disclosure;

FIGS. 8B and 8C are exemplary graphs illustrating an exemplary comparison of $K^{trans}$ and $v_e$ estimations from the exemplary ACE-MRI for a tumor according to an exemplary embodiment of the present disclosure;

Figure 1:
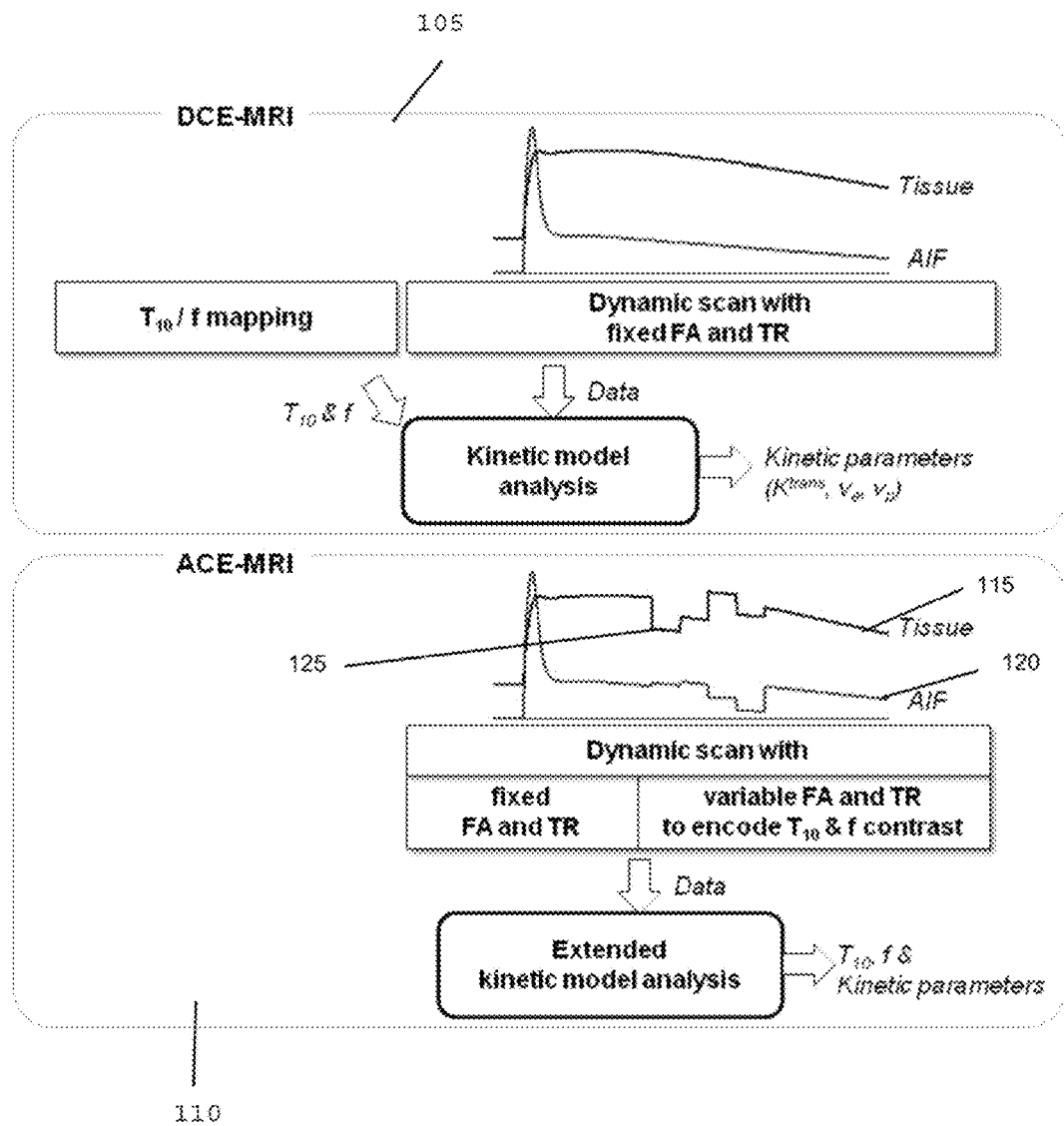
FIG. 1 is an exemplary diagram illustrating an exemplary comparison of DCE-MRI and an exemplary ACE-MRI.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures, and accompanying claims.

DETAILED DESCRIPTION OF EXEMPLARY EMBODIMENTS

Exemplary ACE-MRI

A benefit of the exemplary system, method and computer-accessible medium (e.g., ACE-MRI) can be to eliminate the need to spend extra scan time to measure f and $T_{10}$ parameters in DCE-MRI experiments. Conventional DCE-MRI studies with quantitative contrast kinetic analyses utilize considerable extra time for f and $T_{10}$ measurements in addition to the actual dynamic scan. The measured f and $T_{10}$ maps, with different field of view or spatial resolutions, can be co-registered and/or resampled to match with the dynamic images for a quantitative kinetic model analysis. In the exemplary ACE-MRI, the f and $T_{10}$ mapping procedures can be embedded within the dynamic scan such that there can be no extra scan time needed to the measurement of f and $T_{10}$ maps. This combination can be achieved by utilizing the slow-varying, wash-out portion of the DCE-MRI curve to actively encode the signal intensity with different FAs and TRs, referred to as active contrast encoding.

An exemplary diagram illustrating an exemplary comparison of DCE-MRI 105 and an exemplary ACE-MRI 110 is shown in FIG. 1. The actual FA achieved in a DCE-MRI scan can be affected by various factors, such as B1 field inhomogeneity (see, e.g., Reference 23), RF pulse profile (see, e.g., Reference 27), nonlinearity of RF amplifier (see, e.g., Reference 28), tissue properties (see, e.g., Reference 19), and imperfect spoiling in steady-state imaging. (See, e.g., Reference 13). Here, it can be assumed that the actual FA (e.g., aFA) can be scaled by a FA correction factor, f, from the nominal FA (e.g., nFA), for example, aFA=f×nFA. f can be $B_1$, or a combination of multiple factors described above. Although f can be assumed to be a constant applicable to all FAs, for simplicity, the exemplary system, method and computer-accessible medium, according to an exemplary embodiment of the present disclosure, can be extended to estimate a higher order relationship between the aFA and the nFA.

The time-intensity curve S(t) of the exemplary ACE-MRI illustrated in FIG. 1 (e.g., curve 115 for tissue, and curve 120 for AIF) shows multiple jump discontinuities 125 introduced by changing the FA and/or the TR for active contrast encoding during the wash-out phase. When a spoiled gradient echo sequence can be used for the exemplary ACE-MRI, S(t) can be expressed, for example, as the following:

$$S(t) = S_0 \frac{(1 - e^{-R_1(t)TR(t)})\sin(f\alpha(t))}{(1 - \cos(f\alpha(t))e^{-R_1(t)TR(t)})} \quad [1]$$

where $R_1(t)$ can be the longitudinal relaxation rate that can be the inverse of $T_1(t)$, and $S_0$ can represent the fully relaxed signal for a 90° pulse when TR>>1/$R_1(t)$ and TE<<$T_2$*. For the exemplary ACE-MRI, both the nominal FA ($\alpha$) and the TR may not be fixed constants, but can be functions of time for active contrast encoding, which can be, for example:

$$\alpha(t) = \begin{cases} \alpha_1, 0 \le t < t_1 \\ \alpha_2, t_1 \le t < t_2 \\ \vdots \\ \alpha_N, t_{N-1} \le t \le t_N \end{cases}, \text{ and} \quad [2]$$

$$TR(t) = \begin{cases} TR_1, & 0 \le t < t_1 \\ TR_2, & t_1 \le t < t_2 \\ \vdots \\ TR_N, & t_{N-1} \le t \le t_N \end{cases}, \quad [3]$$

where N can be the number of segments with different T1-weighted contrasts. FIG. 2A shows an example with N=7, $t_i$={205, 225, 245, 265, 285, 353, 390} s, $\alpha_i$={10, 12, 8, 5, 2, 90, 10} degrees, and $TR_i$={12, 12, 12, 12, 12, 100, 12} ms. As shown in in FIG. 2A, points 205, indicated by crosses, are longitudinal relaxation rate $R_1(t)$ estimated using the assumption that the baseline scan protocol can be used over the entire duration of the scan. The baseline protocol parts ($\alpha$=10 degrees and TR=12 ms) before and after the parts with other $\alpha$ or TR values, are connected by line 210, which can be used as an approximation of the true $R_1(t)$ curve.

$R_1(t)$ can be calculated from Eq. 1 when f and $R_1(0)=1/T_{10}$ can be provided. In the exemplary ACE-MRI, both f and $T_{10}$ can be estimated simultaneously with $R_1(t)$ by minimizing the discontinuities in the estimated $R_1(t)$. Note that the actual contrast agent concentration, C(t), can remain as a continuous function regardless of such discontinuities in S(t) induced by the active contrast encoding mechanism, and so continuity of the function can be also assumed for $R_1(t)$ which can be determined by C(t). In fast exchange limit, $R_1(t)=1/T_{10}+r_1 C(t)$ where $r_1$ can be the contrast agent longitudinal relaxivity. When the water exchange may not be in the fast exchange limit, $R_1(t)$ may not be linearly proportional to C(t), but can still remain as a continuous function naturally. Thus, continuity of $R_1(t)$ can be a valid assumption for most dynamic scans with contrast agents at any concentration level.

An estimated $R_1(t)$ using a set off and $T_{10}$ estimates, $\hat{R}_1(t)$, can be assessed for its continuity by measuring the jumps at discontinuous points between different contrast encoding parts (e.g., model-free approach) or by comparing it with a contrast kinetic model (e.g., model-based approach). The exemplary model-free approach can be used to estimate f and $T_{10}$ as a separate procedure (e.g., using the same dynamic scan data) performed prior to running a contrast kinetic model analysis, whereas the exemplary model-based approach can be a combined analysis to estimate f, $T_{10}$, and kinetic model parameters together. One, or a combination, of these two methods can be used depending on the specific needs of the various applications.

The exemplary model-free approach can be used when measuring arterial input functions directly from blood vessels, or indirectly from reference regions, such as in muscle. It can also be used to generate f and $T_{10}$ maps independently from a contrast kinetic model analysis. This can be accomplished by using, for example, the same nominal FA for the baseline and wash-in phases as well as at the end of the wash-out phase (e.g., $\alpha_1=\alpha_N$ and $TR_1=TR_N$) as shown in FIG. 2A, while different FAs and TRs can be used for the rest of the wash-out phase. The washout portion of the time-intensity curve can be approximated as a linear line that can connect the beginning and end parts of the wash-out phase with the same baseline FA and TR. Such linear approximation can be acceptable in many cases; a monotonically decreasing linear trend can often be observed in the second half of arterial input functions. (See, e.g., References 10, 30 and 31). Muscle tissue can show a slowly increasing trend, or an almost constant level, in the later portion of time-intensity curve. (See, e.g., References 32 and 33). For the exemplary ACE-MRI, the function with a linear approximation for the wash-out phase can be noted as $\tilde{R}_1$. f and $T_{10}$ can be estimated, for example, as follows:

$$\{\hat{f}, \hat{T}_{10}\} = \arg \min \Sigma_t (\tilde{R}_1(t)|_{f,T_{10}} - \hat{R}_1(t)|_{f,T_{10}})^2. \quad [4]$$

This exemplary model-free method can be more generalized to any shape of wash-out phase by alternating between the baseline protocol (e.g., $\alpha_1$, $TR_1$) and a contrast encoding protocol (e.g., $\alpha_i$, $TR_i$), as shown by the graph in FIG. 2B. FIG. 2B shows an example with N=11, $t_i$={205, 215, 225, 235, 245, 255, 265, 275, 285, 353, 390} s, $\alpha_i$={10, 12, 10, 8, 10, 5, 10, 2, 10, 90, 10} degrees, and $TR_i$={12, 12, 12, 12, 12, 12, 12, 12, 12, 100, 12} ms. As shown in FIG. 2B, points 215, points indicated by crosses, are longitudinal relaxation rate $R_1(t)$ estimated using the assumption that the baseline scan protocol can be used over the entire duration of the scan. The baseline protocol parts ($\alpha$=10 degrees and TR=12 ms) are connected by line segment 220, which can be used as an approximation of the true $R_1(t)$ curve. In this exemplary manner, this exemplary model-free approach can assume only a piece-wise linearity during one segment of contrast encoding parts and can be used for all cases. $\hat{R}_1(t)|_{\hat{f},\hat{T}_{10}}$ can be used for further analysis with any contrast kinetic model.

The exemplary model-based procedure may not need to use any assumption about the linearity of the curve. Instead, it can utilize a contrast kinetic model of C(t) which can be a continuous function. For instance, C(t) can be modeled using the extended generalized kinetic model with a vascular compartment (see, e.g., Reference 9), which can be, for example:

$$c_t(t) = v_p C_p(t) + K^{trans} \int_0^t C_p(u) \exp\left(-\frac{K^{trans}}{v_e}(t-u)\right) du \quad [5]$$

where $C_p(t)$ can be the contrast concentration in the plasma. These kinetic model parameters can be estimated together, for example, with f and $T_{10}$ as follows:

$$\{\hat{f}, \hat{T}_{10}, \hat{K}^{trans}, \hat{v}_e, \hat{v}_p\} = \arg \min \Sigma_t ((1/T_{10}+r_1 C_t(t)) - \hat{R}_1(t)|_{f,T_{10}})^2 \quad [6]$$

The parameter estimation procedure shown in Eqs. 4 and 6 can also be performed using the time-intensity curves, or signal enhancement ratio curves, instead of R1 curves.

The exemplary parameter estimation procedure can also be extended to use transient behavior of the MRI signal in between changes of the scan protocol based on magnetic resonance spin dynamics. FIGS. 2C and 2D show exemplary signal enhancement ratio curves (e.g., crosses 225) corresponding to the data shown in FIGS. 2A and 2B. Lines 230 represent exemplary contrast kinetic model fits to the signal enhancement ratios (crosses) with additional parameters, such as f and $T_{10}$. The exemplary arterial input function (AIF), $C_p(t)$, is shown in the inset.

The exemplary encoding procedure can be made to estimate other parameters (e.g., proton density, magnetic field ("$B_0$") and transverse relaxation time ("$T_2^*$")) based on active encoding of the signal intensity with FAs, TRs and echo times of the pulse sequence. The exemplary encoding procedure can also be made to estimate proton densities, $T_{10}$ and $T_2^*$ values of multiple tissue components (e.g., water and fat) within an imaging voxel.

The exemplary encoding procedure can be utilized during acquisition of a DCE-MRI signal. It can be based on a slow-varying wash-out portion of a dynamic contrast enhanced magnetic resonance imaging scan. The wash-out portion can be approximated using a contrast agent kinetic model, or as a linear line(s) that can connect a start and an end of an encoding duration with a baseline flip angle and a baseline repetition time. The tissue(s) can be any tissue with capillaries that can allow extravasation of contrast agents.

Exemplary Simulation Study

A numerical simulation study was conducted to assess the feasibility of using the exemplary ACE-MRI to estimate f and $T_{10}$ along with contrast kinetic parameters. The exemplary model-based approach was used for the simulation study since it can be a more challenging case than the exemplary model-free approach due to a greater number of parameters to simultaneously estimate. Both DCE-MRI data and the exemplary ACE-MRI data were generated using the extended generalized kinetic model (e.g., Eq. 5) with an arterial input function ("AIF"), Cp(t), obtained from a previous 7T mouse study. (See, e.g., Reference 34). It was assumed that the actual FA was affected by a scaling factor f for all angles. For the conventional DCE-MRI data, fixed TR (e.g., about 7.5 ms) and α (about 15°) were used. For the exemplary ACE-MRI data generation, both α and TR were varied to encode various $T_1$ weighting contrasts as defined above for FIGS. 2A and 2C. Rician noise with signal-to-noise ratio ("SNR") of about 10 or 20 was added to S(t). SNR was defined as the ratio of the baseline signal to the standard deviation of the Gaussian noise applied to the imaginary and real part of the complex data assuming the simulated MRI signal was the real part of complex MRI data. Temporal resolution was about 5 s/frame for small flip angles and about 45 s/frame for a 90 degree FA.

The baseline contrast kinetic parameters for simulation were $K^{trans}$=0.2505(/min), $v_e$=0.45, and $v_p$=0.06. (See, e.g., Reference 35). The baseline f and $T_{10}$ were about 1 and 2.3 s, respectively. To evaluate the performance of the exemplary ACE-MRI in a variety of conditions, the simulation study was repeated by changing one parameter at a time as shown in Table 1 below. Simulations were also conducted to assess the influence of different FAs and TRs on the estimation result, in order to determine the range of FA and TR values to be used for the exemplary ACE-MRI experiments. Parameter estimation was conducted using the Simplex method provided in Matlab (e.g., MathWorks, Natick, Mass.). (See, e.g., Reference 36). The exemplary result of parameter estimation with noisy data can be sensitive to initial values. Thirty randomly selected initial guesses were used for each noisy time-intensity curve. The result with the minimum sum of squares of the differences was selected as the final result. Accuracy of the estimated parameters was measured by the difference between the mean estimated value and the true value used for data simulation. Precision was assessed in terms of coefficient of variation (e.g., CV=standard deviation/mean). The average of accuracy and precision measures was used as measure of uncertainty.

TABLE 1

Parameters used for the simulation study

| Parameters | $K^{trans}$ (/min) | $v_e$ | $v_b$ | $B_1$ | $T_1$ (s) |
|---|---|---|---|---|---|
| $K^{trans}$ (/min) | 0.05, 0.15, 0.25, 0.35, 0.45 | 0.45 | 0.06 | 1.0 | 2.3 |

TABLE 1-continued

Parameters used for the simulation study

| Parameters | $K^{trans}$ (/min) | $v_e$ | $v_b$ | $B_1$ | $T_1$ (s) |
|---|---|---|---|---|---|
| $v_e$ | 0.25 | 0.15, 0.25, 0.35, 0.45, 0.55 | 0.06 | 1.0 | 2.3 |
| $v_b$ | 0.25 | 0.45 | 0.03, 0.06, 0.09, 0.12, 0.15 | 1.0 | 2.3 |
| $B_1$ | 0.25 | 0.45 | 0.06 | 0.8, 0.9, 1.0, 1.1, 1.2 | 2.3 |
| $T_1$ (s) | 0.25 | 0.45 | 0.06 | 1.0 | 1.4, 1.7, 2.0, 2.3, 2.6 |

* Numbers in bold are baseline values.

Exemplary In Vivo ACE-MRI

Six- to eight-week-old C57BL/6 mice (e.g., n=10) were given a subcutaneous/intracerebral injection of 1×10⁵ GL261 mouse glioma tumor cells, suspended in about 0.1 mL of phosphate-buffered saline. Mice were scanned on post-injection day 14-21 when tumors were observed. For MRI scans, general anesthesia was induced by about 1.5% isoflurane in air. The animal body temperature was maintained at about 34±2° C. during the scan.

MRI experiments were performed on a 7T micro-MRI system, consisting of a Biospec Avance II console (e.g., Bruker Biospin MRI, Ettlingen, Germany) interfaced to a 200-mm horizontal bore magnet (e.g., Magnex Scientific, Yarnton, Kidlington, Oxfordshire, UK) with an actively shielded gradient coil (e.g., Bruker, BGA-95; gradient strength, 750 mT/m). A quadrature Litz coil (e.g., Doty Scientific, Columbia, S.C., USA) was used to image the animal mounted on a cradle with respiratory and temperature monitoring probes.

Prior to the dynamic study, a $T_1$ measurement was performed using a RARE VTR pulse sequence with multiple TRs and TEs for cross-validation of $T_{10}$ measured from the exemplary ACE-MRI. The $B_1$ field was also measured using the 180° signal null ("SN") method (see, e.g., Reference 23) with TR=1s and three flip angles of 140°, 150° and 160°. A three-dimensional ("3D") FLASH sequence was used for dynamic scans using the exemplary ACE-MRI. Scan parameters were TE=3.83 ms, image matrix=100×100×9, and resolution=0.15×0.15×1 mm. This sequence was run to acquire 78 3D images for about 9 minutes with multiple FAs (e.g., 10°, 12°, 8°, 5°, 2°, 90°, and 10°) and different number of repetitions (e.g., 50, 5, 5, 5, 5, 3, and 5, respectively). TR was about 100 ms when FA=90° and about 12 ms for the other flip angles. Temporal resolution was about 5.4 s/frame for small FAs and about 45 s/frame when FA=90°. A bolus of about 10 mM Gd-DTPA in saline, corresponding to dose 0.1 mmol/kg, was injected through a tail vein catheter, starting about 1 min after the acquisition of pre-contrast images.

AIF was obtained from a reference region in the muscle (see, e.g., Reference 37) based on the f and $T_{10}$ values estimated by using the exemplary model-free approach. The Gd concentration in the capillary plasma, $C_p(t)$, was estimated from that of a reference tissue, $C_{tis}(t)$, using the following exemplary equation: $C_p(t)=C_{tis}(t)/v_e+(1/K^{trans})$ $dC_t(t)/dt$. $K^{trans}$ and $v_e$ of the muscle were assumed to be about 0.11 min⁻¹ and 0.15, respectively. (See, e.g., Reference 37). In order to minimize the effect of the noise, a multiple layer neural network with 1 by 2 neurons in each hidden layer was used to fit to the tissue concentration curve. For the rest of the images, both the exemplary model-free and the exemplary model-based methods were used to estimate 5 free parameters (e.g., $K^{trans}$, $v_e$, $v_p$, f and $T_{10}$) as described above.

Exemplary Statistical Analysis

Accuracy of the estimated parameters was measured by the difference between the median of estimated value and the true value used for data simulation. Precision was assessed in terms of coefficient of variation ("CV"=standard deviation/mean).

Wilcoxon rank sum test was used to test the difference in accuracy or precision between the parameters measured by using the exemplary ACE-MRI and separate scans using SN and RARE VTR. A p-value of less than about 0.05 was considered significant.

Exemplary Results

Exemplary Comparison Between DCE-MRI and ACE MRI

Figure 3A:
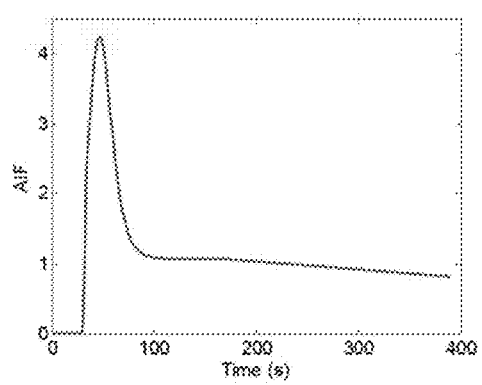
FIGS. 3A-3D are exemplary graphs illustrating an exemplary estimation of f, and $T_{10}$, and contrast kinetic parameters from DCE-MRI and the exemplary ACE-MRI.
Figure 3B:
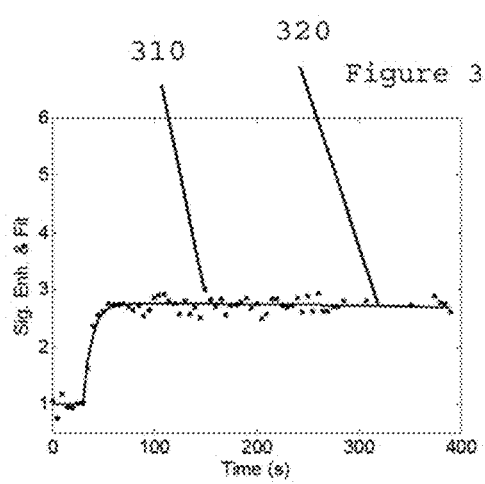
Figure 3C:
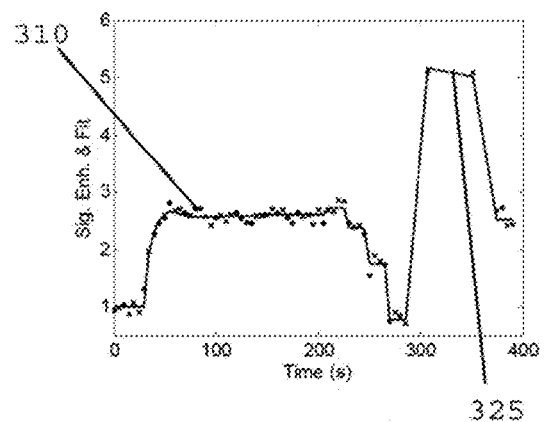
Figure 3D:
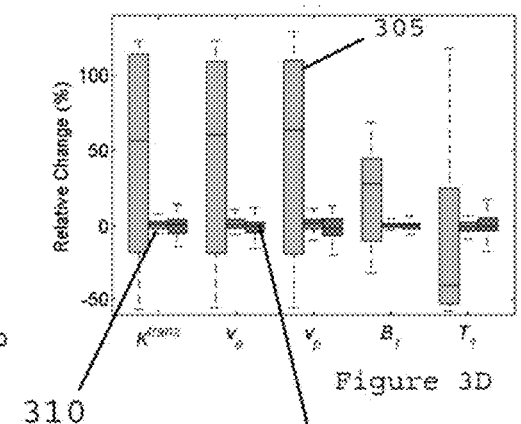

FIGS. 3A-3D show exemplary graphs providing a comparison of a conventional DCE-MRI data (e.g., points 305 in FIG. 3B) and the exemplary ACE-MRI data (e.g., points 310 in FIG. 3C) generated using the baseline kinetic parameters provided in Table 1 above, and also demonstrate that the exemplary ACE-MRI can be used to simultaneously estimate the contrast kinetic parameters, f and $T_{10}$. FIG. 3A illustrates an exemplary arterial input function used to simulate data points shown in FIGS. 3B and 3C. The GKM fitting with f and $T_{10}$ parameters can be performed with a reasonable good fit for both DCE-MRI (e.g., line 320 in FIG. 3B) and the exemplary ACE-MRI data (e.g., line 325 in FIG. 3C) as shown in FIGS. 3B and 3C, respectively. However, inclusion of f and $T_{10}$ in the GKM fitting to the DCE-MRI data led to substantially large uncertainty in the estimated parameters as shown by bars 305 in FIG. 3D, as DCE-MRI time-intensity curves do not provide enough information for estimation of f and $T_{10}$. In contrast, the model fitting with the exemplary ACE-MRI data was able to estimate the kinetic model parameters, as well as f and $T_{10}$, with better accuracy and precision as shown by boxes 310 and 315 in FIG. 3D; relative median errors were less than about 3% for all five parameters. It is noted that the relative errors did not increase noticeably when the SNR decreased from 20 to 10.

Exemplary Flip Angle Correction Factor (f)

The simulation data was also used to assess the effect of the large FA used for the active contrast encoding on the uncertainty in estimation of f. The last FA $\alpha_6$ varied from about 30° to about 90° while all the other scan parameters were kept the same and the baseline kinetic parameters were used (e.g., see FIG. 4A which shows multiple lines 405 that correspond to the time-intensity curves simulated with $\alpha_6$=30-90°). Boxes 410, shown in FIGS. 4 B-4F, illustrate the median and inter-quartile range ("IQR") of estimated parameters ($K^{trans}$, $v_e$, $v_p$, f, and $T_{10}$, respectively) for different FA $\alpha_6$ values between about 30° and about 90°. When $\alpha_6$=30°, the IQR of f was from about 0.70 to 1.33. The f-IQR decreased substantially as $\alpha_6$ increased to 90° (e.g., IQR=0.98-1.02). Similar patterns were observed with other parameters. FIGS. 4B-4F demonstrate that accurate estimation of f can be beneficial since it affects the estimation of all the other parameters; the estimated f can be used to adjust the FA that can affect the estimation of $T_{10}$ as well as the kinetic parameters. Use of a large FA for f estimation can utilize a longer TR to minimize the specific absorption rate ("SAR") effect. The effect of TR on the parameter uncertainty was evaluated by changing TR from about 15 ms to about 90 ms for $\alpha_6$=90°. The IQR remains within about 5.3% over the range of TR values investigated, suggesting that the selection of TR does not noticeably change the uncertainty of the parameter estimation (e.g., see FIG. 5A-5F). FIG. 5A illustrates multiple lines 505 that correspond to the time-intensity curves simulated with TR=15-90 ms. Boxes 510 in FIGS. 5B-5F show the median and IQR of estimated parameters ($K^{trans}$, $v_e$, $v_p$, f, and $T_{10}$, respectively) for different TR values between about 15 ms and about 90 ms.

Exemplary Uncertainty in Parameter Estimation

Figure 6I:
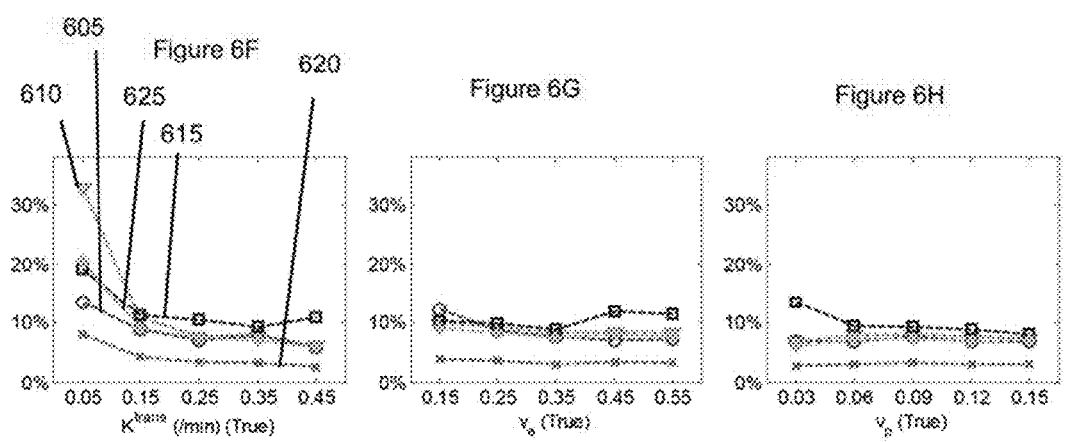
Figure 6J:
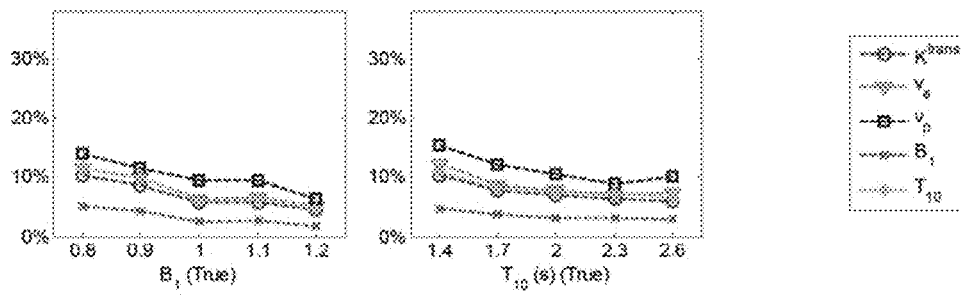
Figure 6N:
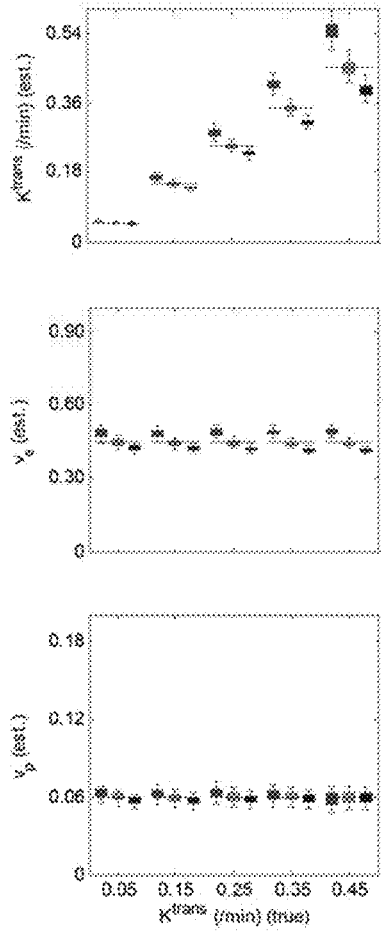
FIGS. 6N-6P are exemplary graphs illustrating further accuracy and precision of contrast kinetic parameters from DCE-MRI based on the uncertainty of $B_1$ measurement.
Figure 6O:
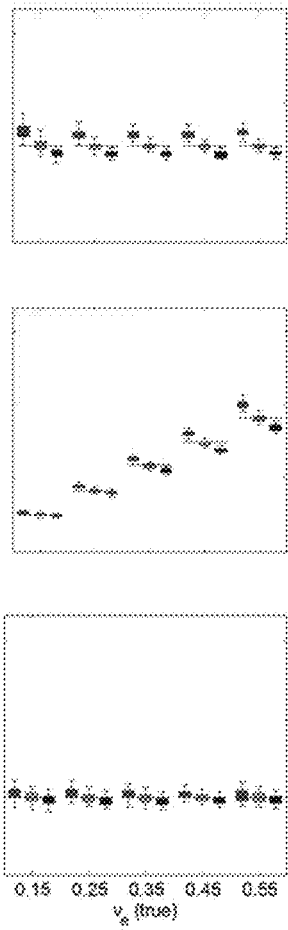
Figure 6P:
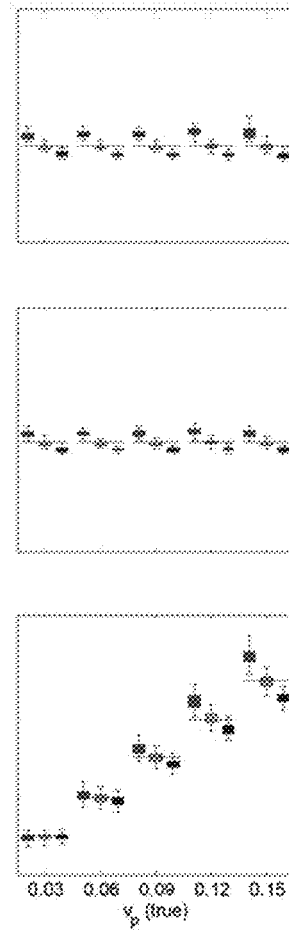

FIGS. 6A-6J show exemplary graphs providing accuracy and precision of the f, $T_{10}$, and contrast kinetic parameters estimated by fitting a contrast kinetic model to the simulated data (e.g., the exemplary model-based approach) with SNR=10. Each column of plots illustrated in FIG. 6A-6E represents a set of cases where one parameter was varied while the other parameters were held constant. The graphs of FIGS. 6A-6C show that the variation in the contrast kinetic parameters does not have any noticeable effect on the measurement of f (e.g., median: 1.00, IQR: 0.98-1.03) and $T_{10}$ (e.g., median: 2.27, IQR: 2.15-2.39). The worst case to estimate f and $T_{10}$ was when $K^{trans}$ was 0.05 min-1, the lowest in this study as the median f=1.00 (e.g., IQR: 0.94-1.02) and median $T_{10}$=2.35 (e.g., IQR: 2.19-2.64). The CV (e.g., IQR/median) of parameters increased up to 33% when $K^{trans}$ decreased from 0.15 to 0.05 min-1 (e.g., FIG. 6F, which illustrate $K^{trans}$ 605, $v^e$ 610, $v_p$ 615, B1 620, and $T_{10}$ 625, whereas the same identifiers are provided in FIGS. 6G-6J). In terms of CV shown in FIG. 6F-6J (e.g., IQR/median of data shown in FIG. 6A-6E), the variation of the true f and $T_{10}$ (e.g., see FIGS. 6D and 6E) also did not have any noticeable effect on the estimation accuracy of other parameters. The CV of contrast kinetic parameters decreased as f and $T_{10}$ increased; (e.g., 10-14% when f=0.8, and 4-6% when f=1.2; 10-15% when $T_{10}$=1.4 s and 6-10% when $T_{10}$=2.6).

The uncertainties of the exemplary ACE-MRI parameters measured with the simulated data were compared with those of DCE-MRI data using f and $T_{10}$ containing no error or 10% error (e.g., see FIGS. 6K-6P). f was assumed to be the same as $B_1$ in this case. Table 2 below summarizes the accuracy and precision of parameters estimated using the exemplary ACE-MRI in comparison with those from DCE-MRI. The errors of ACE-MRI kinetic parameters (e.g., 5.8-8.6%) were about twice as big as the errors of DCE-MRI kinetic parameters using accurate f and $T_{10}$ with no error (e.g., 2.0-5.1%), but about half of the errors with 10% error in either f or $T_{10}$ (e.g., 10.7-14.8%).

TABLE 2

Uncertainties of kinetic parameters estimated using conventional DCE-MRI data with 0% or 10% error in either $B_1$ or $T_{10}$, based on the data presented in FIGS. 6K-6P. These uncertainties in DCE-MRI are compared with those of the exemplary ACE-MRI in which $B_1$ and $T_{10}$ are estimated together with the kinetic model parameters.

| | $K^{trans}$ (min$^{-1}$) | | $v_e$ | | $v_p$ | |
|---|---|---|---|---|---|---|
| | Error (%) | CV (%) | Error (%) | CV (%) | Error (%) | CV (%) |
| DCE (0% error in $T_{10}/B_1$) | 2.65 ± 2.01 | 4.06 ± 1.93 | 2.00 ± 1.52 | 4.21 ± 1.64 | 5.10 ± 3.79 | 3.51 ± 1.41 |

TABLE 2-continued

Uncertainties of kinetic parameters estimated using conventional DCE-MRI data with
0% or 10% error in either $B_1$ or $T_{10}$, based on the data presented in FIGS. 6K-6P. These
uncertainties in DCE-MRI are compared with those of the exemplary ACE-MRI in which $B_1$ and
$T_{10}$ are estimated together with the kinetic model parameters.

| | $K^{trans}$ (min$^{-1}$) | | $v_e$ | | $v_p$ | |
|---|---|---|---|---|---|---|
| | Error (%) | CV (%) | Error (%) | CV (%) | Error (%) | CV (%) |
| DCE (10% error in $T_{10}/B_1$) | 14.83 ± 9.98 | 4.13 ± 1.91 | 12.44 ± 7.20 | 6.09 ± 4.33 | 10.68 ± 6.90 | 3.56 ± 1.38 |
| ACE | 5.84 ± 4.17 | 7.65 ± 2.54 | 6.66 ± 4.74 | 7.58 ± 2.48 | 8.65 ± 6.16 | 6.84 ± 2.15 |

Exemplary In Vivo Mouse Imaging

Figure 7A:
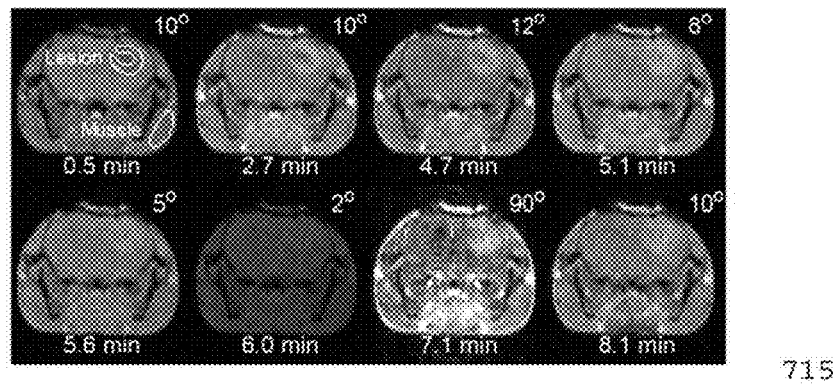
FIG. 7A is a set of exemplary ACE-MRI images at different time points with different flip angles and different TRs according to an exemplary embodiment of the present disclosure.
Figure 7B:
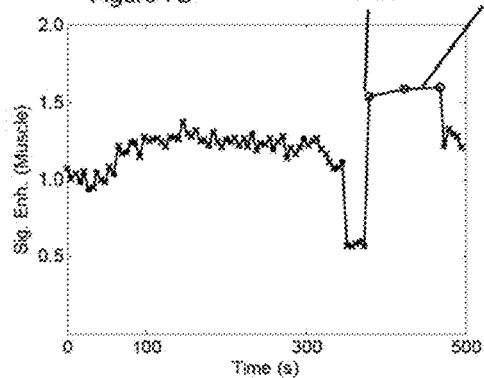
FIGS. 7B and 7C are diagrams of exemplary signal enhancement curves according to an exemplary embodiment of the present disclosure.
Figure 7C:
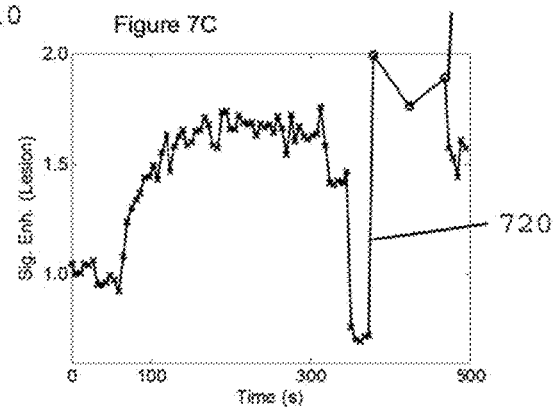
Figure 7D:
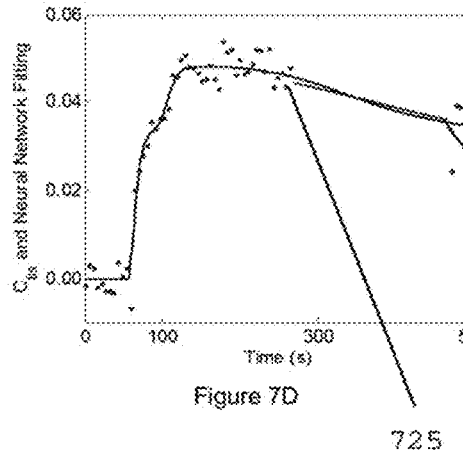
FIG. 7D is an exemplary graph illustrating neural network fitting according to an exemplary embodiment of the present disclosure.
Figure 7E:
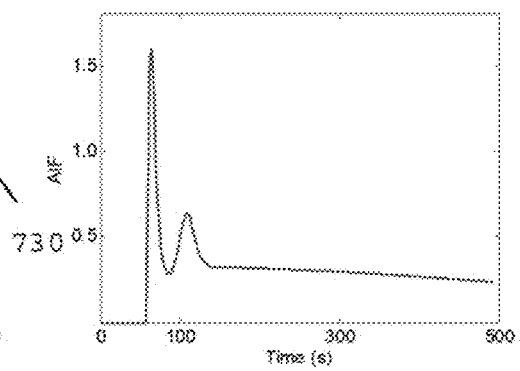
FIG. 7E is an exemplary graph illustrating an estimated arterial input function according to an exemplary embodiment of the present disclosure.

The exemplary ACE-MRI was also tested for in vivo mouse imaging. FIG. 7A shows exemplary images of a mouse scanned with the exemplary ACE-MRI with multiple FAs. FIG. 7B shows an exemplary signal enhancement ratio curve from the muscle region shown in the first image of FIG. 7A. Points 705 are connected by lines 710, which show the trend more clearly. The muscle data shown in FIG. 7B were used to estimate the arterial input function shown in FIG. 7E. FIG. 7C shows an exemplary signal enhancement ratio curve from the lesion shown in the first image of FIG. 7A. Points 715 are connected by lines 720, which show the trend more clearly. FIG. 7D shows data with the baseline protocol (e.g., points 725) and a contrast kinetic model fit (e.g., line 730). Line 725 line is a straight line connecting the adjacent data with the baseline protocol. As described above, both the exemplary model-free and the exemplary model-based methods can be applied to the same data set.

FIGS. 8A-8C illustrate exemplary results from applying the exemplary model-free method for estimation of f and $T_{10}$ without using any kinetic model. The estimated f map or images (e.g., shown in FIG. 8A) was comparable with the B1 map measured with the SN (see, e.g., Reference 22) and the slice profile correction. (See, e.g., Reference 27). The estimated $T_{10}$ map (e.g., illustrated in FIG. 8A) was also found to be in agreement with the $T_1$ map obtained from an inversion recovery sequence with multiple inversion times. The exemplary scatter plots in FIGS. 8B and 8C show that the $K^{trans}$ and $v_e$ values estimated from the exemplary ACE-MRI model-free method matches well with those from the conventional independent measurements of the corresponding parameters. FIG. 8A also shows the results of kinetic model analysis using the f and $T_{10}$ values estimated from the exemplary model-free method. The pixels maps of the kinetic model parameters are well regularized despite no data smoothing being used, which substantiates that the parameter estimation was robust.

Figure 9A:
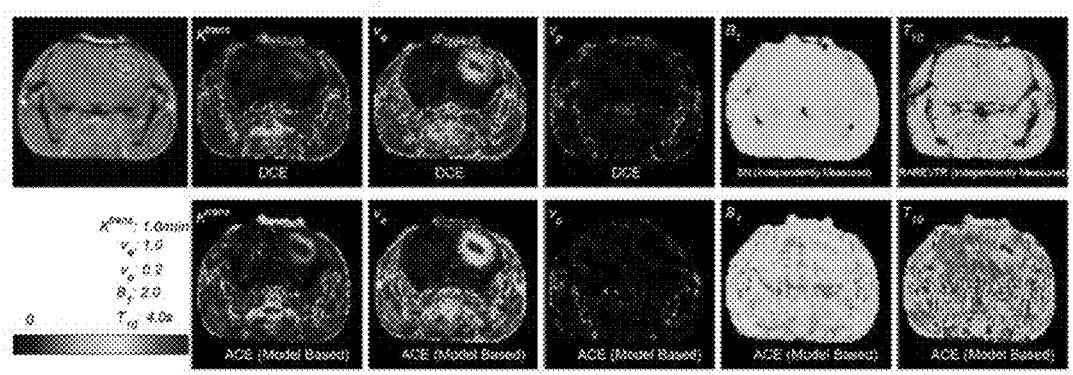
FIG. 9A is a set of exemplary images of in-vivo data processing using an exemplary model-based procedure according to an exemplary embodiment of the present disclosure.
Figure 9B:
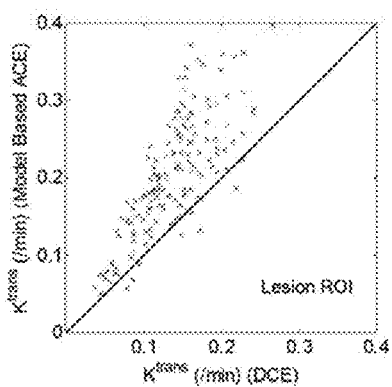
FIGS. 9B and 9C are exemplary graphs illustrating $K^{trans}$ and $v_e$ estimations from the exemplary ACE-MRI according to an exemplary embodiment of the present disclosure.
Figure 9C:
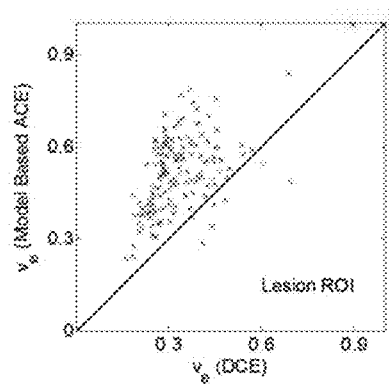

FIGS. 9A-9C show exemplary results from an application of the model-based approach where estimation of f, $T_{10}$ and kinetic model parameters was simultaneously conducted. All the parameter maps shown in FIG. 9A appear comparable with the corresponding ones in FIG. 8A. The f and $T_{10}$ values estimated using the exemplary mode-based method were also close to the individually measured $B_1$ and $T_1$ values from the SN and RARE-VTR methods.

Exemplary Discussion

Contrast kinetic model analysis of DCE-MRI data has been used as a means to quantitatively assess tumor microcirculation environment for diagnosis of tumor and monitoring treatment response. However, its application can often be hampered by the need to have accurate $B_1$ and $T_{10}$ information, which usually takes an additional long scan time for measurement of $B_1$ and $T_{10}$. In addition, the actual FA can be affected by factors other than $B_1$ which further complicates the analysis of DCE-MRI data. As a result, the utility of contrast kinetic model analysis of DCE-MRI can be limited despite its high potential.

The exemplary ACE-MRI can be used to estimate the flip angle correction factor f and $T_{10}$, simultaneously, along with the contrast kinetic model parameters, without using any additional scan dedicated to measure f and $T_{10}$. Numerical simulation data was used to show that the active contrast encoding during the wash-out phase of a dynamic scan can enable estimation of f and $T_{10}$. The uncertainty in the parameter estimation using the exemplary ACE-MRI was smaller than that of conventional DCE-MRI using f and $T_{10}$ with 10% error. The exemplary ACE-MRI can also be used for imaging any tissue with a capillary permeable to contrast agents as demonstrated by a mouse model of breast cancer at 7T. The estimated contrast kinetic parameters are well regularized while clearly delineating the lesion, indicating that the contrast kinetic model fitting to the exemplary ACE-MRI data was robust. The f and $T_{10}$ estimated from the exemplary ACE-MRI data matched well with the $B_1$ and $T_1$ measured using the dedicated pulse sequences.

While $B_1$ and $T_1$ can be measured separately, they can also be measured simultaneously as a measurement of one parameter can be closely related with the other. It has been shown that shown that variable FA data and inversion recovery data can be used together to estimate $B_1$ and $T_1$ by fitting the signal models of two experiments that include the $B_1$ and $T_1$ parameters. (See, e.g., Reference 20). Using this approach, known as DESPOT1-HIFI (e.g., Driven Equilibrium Single Pulse Observation of T1 with High-speed Incorporation of RF field Inhomogeneities), and the exemplary ACE-MRI, both $T_1$ and $B_1$ can be estimated when the data is sufficiently encoded with various $T_1$ and $B_1$ weighted contrasts. While DESPOT1-HIFI uses an inversion recovery pulse sequence as an additional parameter, the exemplary ACE-MRI protocol uses the data with, e.g., a 90° FA and a longer TR. The exemplary ACE-MRI can be further extended to estimate multicomponent $T_1$ and $T_2$, as well as $B_0$ and $B_1$, by using an array of different contrast images (e.g., gradient echo imaging data with 9 different FAs, inversion recovery imaging data with one inversion time, and balanced steady-state imaging data with 9 FAs which took about 16 min for the whole brain). The exemplary ACE-MRI can also be extended to estimate other parameters simultaneously. This concept of randomized "contrast encoding" used in MRI can also be applied to ACE-MRI for further optimization of the protocol in a future study.

The exemplary ACE-MRI can simplify and shorten MRI exam time as it can provide comprehensive information about tissue MR properties from a single scan. Breast cancer imaging can be one of the areas suitable for the exemplary ACE-MRI. Screening mammography has been recognized as one of the leading contributors to reducing breast cancer mortality by 30% in last decade. Despite such success of screening mammography, and the recent development of various new approaches to therapy, breast cancer remains the second leading cause of cancer death in women, and the leading cause of death in women aged 45 to 55. (See, e.g., Reference 45). This fact illustrates key limitations in the ability of current screening approaches, largely based on mammography, to detect cancerous lesion at an early stage, particularly in young women with dense breasts. In addition, mammography has well-recognized limitations, such as exposure to ionizing radiation (see, e.g., Reference 46), such that annual screening mammography may not be recommended for women under 40 years old. Coincidentally, the 5-year survival rate of the age group of 20-34 can be 78%, the worst among the age groups. (See, e.g., Reference 47). Previous studies have shown that MRI can be the most accurate diagnostic imaging modality to date, particularly for mammographically occult malignancies in young women with high lifetime risk for breast cancer. (See, e.g., Reference 48). However, current breast MRI protocols are time consuming and costly, such that screening MRI may not be available to all women at high risk for breast cancer. It can therefore be beneficial to improve diagnostic accuracy while shortening exam time, in order to facilitate more women to benefit from breast MRI. The exemplary ACE-MRI can be a good candidate for such an abbreviated exam of the breast since it can be used to extract multiple tissue properties simultaneously. The specific contrast to be encoded in the exemplary ACE-MRI protocol can be tailored to meet the need of a specific application.

Figure 10:
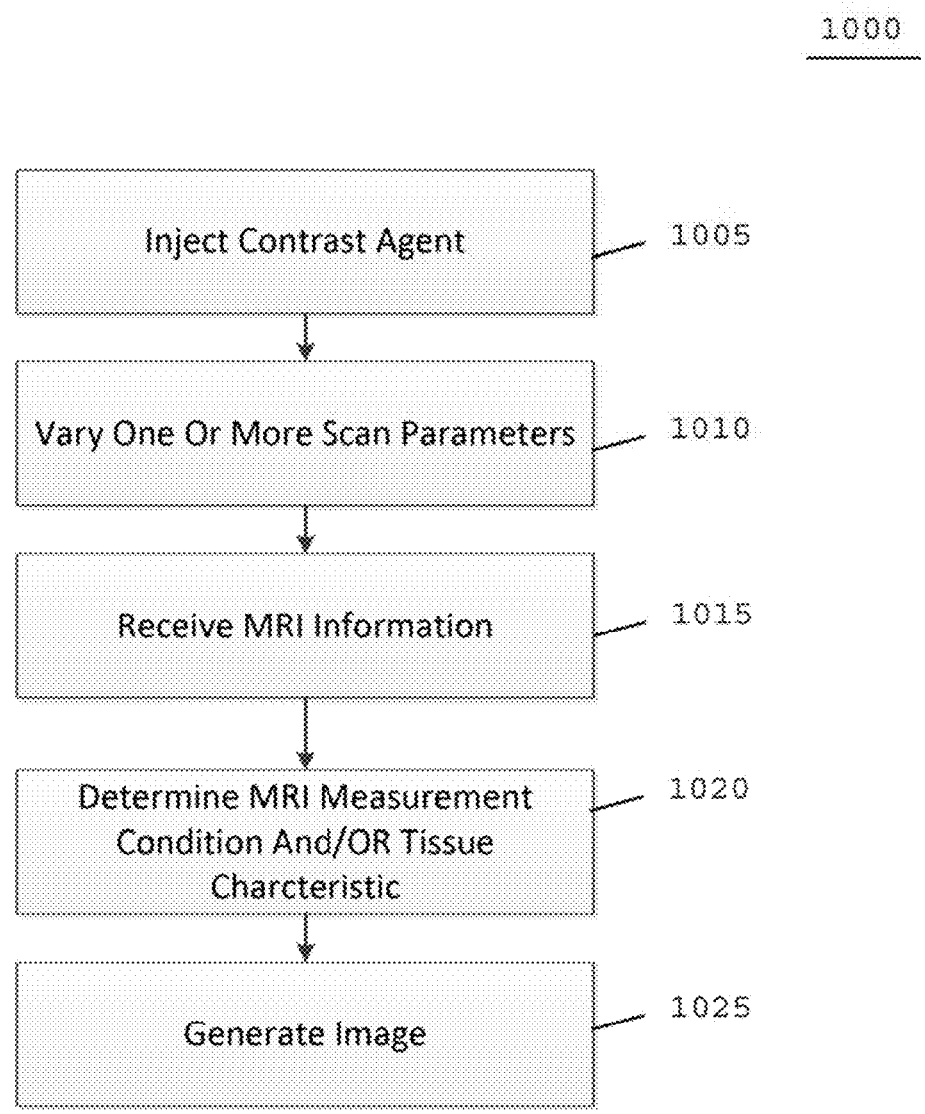
FIG. 10 is a flow diagram of an exemplary method for determining at least one characteristic of a tissue according to an exemplary embodiment of the present disclosure.

FIG. 10 illustrates a flow diagram of an exemplary method 1000 for determining at least one characteristic of a tissue according to an exemplary embodiment of the present disclosure. For example, as shown in FIG. 10, at procedure 1005, a contrast agent can be injected into a patient. At procedure 1010, one or more MRI scan parameters can be varied during all or, a part of, a dynamic MRI scan following the contrast agent injection. At procedure 1015, MRI information of the tissue can be received, and at procedure 1020, a MRI measurement condition and/or a tissue characteristic can be determined, for example, using the exemplary model-based or model-free modes described above. At procedure 1025 an image of the tissue can be generated at procedure.

Figure 11:
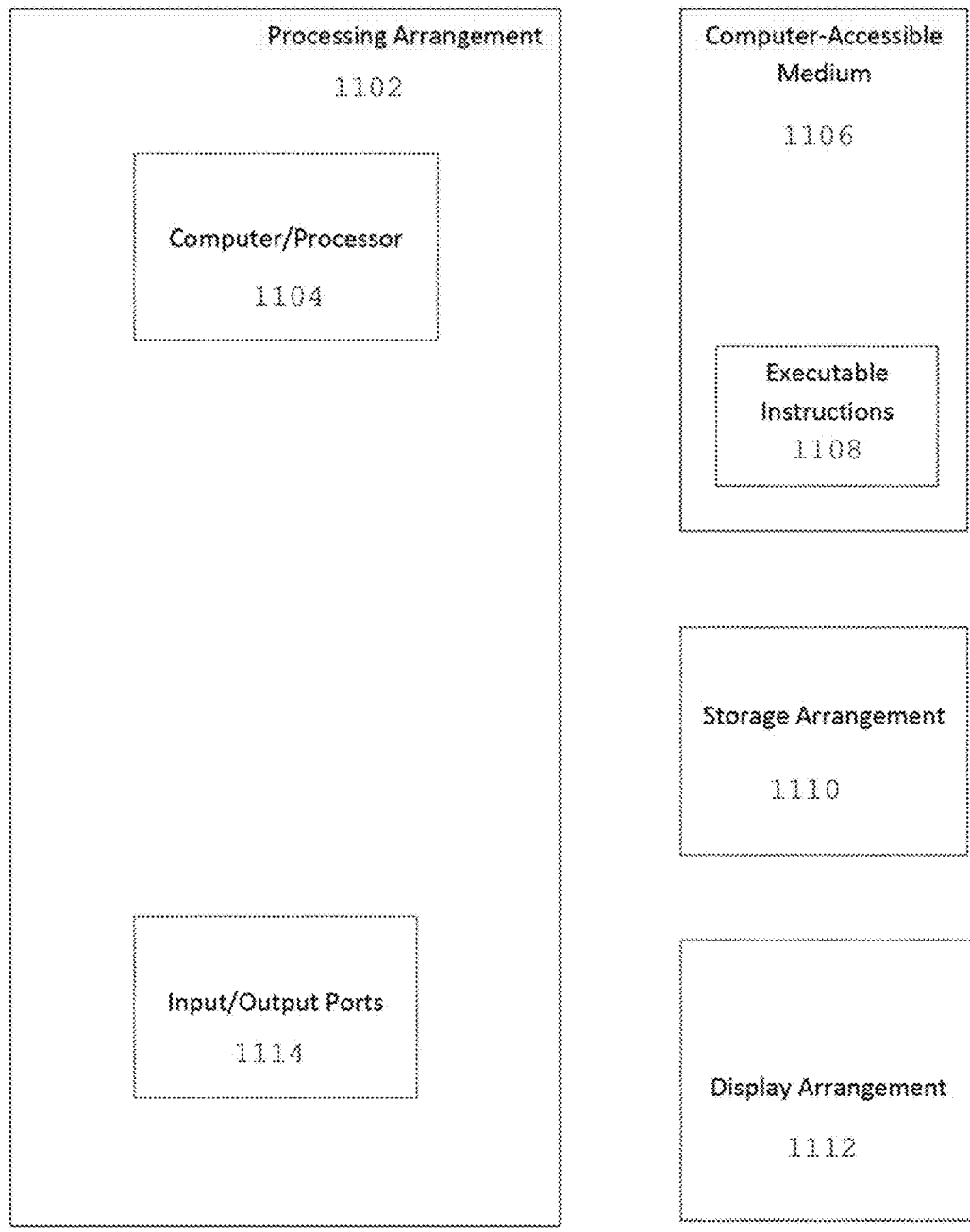
FIG. 11 is an illustration of an exemplary block diagram of an exemplary system in accordance with certain exemplary embodiments of the present disclosure.

FIG. 11 shows a block diagram of an exemplary embodiment of a system according to the present disclosure. For example, exemplary procedures in accordance with the present disclosure described herein can be performed by a processing arrangement and/or a computing arrangement 1102. Such processing/computing arrangement 1102 can be, for example entirely or a part of, or include, but not limited to, a computer/processor 1104 that can include, for example one or more microprocessors, and use instructions stored on a computer-accessible medium (e.g., RAM, ROM, hard drive, or other storage device).

As shown in FIG. 11, for example a computer-accessible medium 1106 (e.g., as described herein above, a storage device such as a hard disk, floppy disk, memory stick, CD-ROM, RAM, ROM, etc., or a collection thereof) can be provided (e.g., in communication with the processing arrangement 1102). The computer-accessible medium 1106 can contain executable instructions 1108 thereon. In addition or alternatively, a storage arrangement 1110 can be provided separately from the computer-accessible medium 1106, which can provide the instructions to the processing arrangement 1102 so as to configure the processing arrangement to execute certain exemplary procedures, processes and methods, as described herein above, for example.

Further, the exemplary processing arrangement 1102 can be provided with or include an input/output arrangement 1114, which can include, for example a wired network, a wireless network, the internet, an intranet, a data collection probe, a sensor, etc. As shown in FIG. 11, the exemplary processing arrangement 1102 can be in communication with an exemplary display arrangement 1112, which, according to certain exemplary embodiments of the present disclosure, can be a touch-screen configured for inputting information to the processing arrangement in addition to outputting information from the processing arrangement, for example. Further, the exemplary display 1112 and/or a storage arrangement 1110 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, e.g., data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entirety.

1. Choyke P L, Dwyer A J, Knopp M V. Functional tumor imaging with dynamic contrast-enhanced magnetic resonance imaging. J Magn Reson Imaging. 2003; 17(5):509-520.
2. Huang W, Li X, Morris E A, Tudorica L A, Seshan V E, Rooney W D, Tagge I, Wang Y, Xu J, Springer C S. The magnetic resonance shutter speed discriminates vascular properties of malignant and benign breast tumors in vivo. Proc Natl Acad Sci USA 2008; 105(46):17943-17948.
3. Kim S, Loevner L A, Quon H, Kilger A, Sherman E, Weinstein G, Chalian A, Poptani H. Prediction of response to chemoradiation therapy in squamous cell carcinomas of the head and neck using dynamic contrast-enhanced MR imaging. AJNR Am J Neuroradiol 2010; 31(2):262-268.
4. Abramson R G, Li X, Hoyt T L, Su P F, Arlinghaus L R, Wilson K J, Abramson V G, Chakravarthy A B, Yankeelov T E. Early assessment of breast cancer response to neoadjuvant chemotherapy by semi-quantitative analysis of high-temporal resolution DCE-MRI: preliminary results. Magnetic resonance imaging 2013; 31(9):1457-1464.
5. Ingrisch M, Sourbron S, Morhard D, Ertl-Wagner B, Kumpfel T, Hohlfeld R, Reiser M, Glaser C. Quantification of perfusion and permeability in multiple sclerosis: dynamic contrast-enhanced MRI in 3D at 3T. Investigative radiology 2012; 47(4):252-258.
6. Hodgson R J, O'Connor P, Moots R. MRI of rheumatoid arthritis image quantitation for the assessment of disease activity, progression and response to therapy. Rheumatology (Oxford) 2008; 47(1):13-21.
7. Mustafi D, Fan X, Dougherty U, Bissonnette M, Karczmar G S, Oto A, Hart J, Markiewicz E, Zamora M. High-resolution magnetic resonance colonography and dynamic contrast-enhanced magnetic resonance imaging in a murine model of colitis. Magn Reson Med 2010; 63(4):922-929.
8. Florie J, Wasser M N, Arts-Cieslik K, Akkerman E M, Siersema P D, Stoker J. Dynamic contrast-enhanced MRI of the bowel wall for assessment of disease activity in Crohn's disease. AJR American journal of roentgenology 2006; 186(5):1384-1392.
9. Tofts P S, Brix G, Buckley D L, Evelhoch J L, Henderson E, Knopp M V, Larsson H B, Lee T Y, Mayr N A, Parker G J, Port R E, Taylor J, Weisskoff R M. Estimating kinetic parameters from dynamic contrast-enhanced T(1)-weighted MRI of a diffusable tracer: standardized quantities and symbols. J Magn Reson Imaging. 1999; 10(3): 223-232.
10. Kim S, Quon H, Loevner L A, Rosen M A, Dougherty L, Kilger A M, Glickson J D, Poptani H. Transcytolemmal water exchange in pharmacokinetic analysis of dynamic contrast-enhanced MRI data in squamous cell carcinoma of the head and neck. J Magn Reson Imaging. 2007; 26(6):1607-1617.
11. Sung K, Daniel B L, Hargreaves B A. Transmit B1+ field inhomogeneity and T1 estimation errors in breast DCE-MRI at 3 tesla. J Magn Reson Imaging. 2013; 38(2):454-459.
12. Nehrke K. On the steady-state properties of actual flip angle imaging (AFI). Magn Reson Med 2009; 61(1):84-92.
13. Yarnykh V L. Optimal radiofrequency and gradient spoiling for improved accuracy of T1 and B1 measurements using fast steady-state techniques. Magn Reson Med 2010; 63(6):1610-1626.
14. Brookes J A, Redpath T W, Gilbert F J, Murray A D, Staff R T. Accuracy of T1 measurement in dynamic contrast-enhanced breast MRI using two- and three-dimensional variable flip angle fast low-angle shot. Journal of magnetic resonance imaging: JMRI 1999; 9(2):163-171.
15. Scheffler K, Hennig J. T(1) quantification with inversion recovery TrueFISP. Magn Reson Med 2001; 45(4):720-723.
16. Look D C, Locker D R. Time saving in measurement of NMR and EPR relaxation times. Review of Scientific Instruments 1970; 41:250.
17. Deoni S C, Rutt B K, Peters T M. Rapid combined T1 and T2 mapping using gradient recalled acquisition in the steady state. Magn Reson Med 2003; 49(3):515-526.
18. Liberman G, Louzoun Y, Ben Bashat D. T-1 Mapping Using Variable Flip Angle SPGR Data With Flip Angle Correction. J Magn Reson Imaging. 2014; 40 (1):171-180.
19. Wang J, Qiu M, Kim H, Constable R T. T1 measurements incorporating flip angle calibration and correction in vivo. J Magn Reson 2006; 182(2):283-292.
20. Deoni S C. High-resolution T1 mapping of the brain at 3T with driven equilibrium single pulse observation of T1 with high-speed incorporation of RF field inhomogeneities (DESPOT1-HIFI). J Magn Reson Imaging. 2007; 26(4):1106-1111.
21. Stollberger R, Wach P. Imaging of the active B1 field in vivo. Magn Reson Med 1996; 35(2):246-251.
22. Insko E K, Bolinger L. Mapping of the Radiofrequency Field. J Magn Reson Ser A 1993; 103(1):82-85.
23. Dowell N G, Tofts P S. Fast, accurate, and precise mapping of the RF field in vivo using the 180 degrees signal null. Magn Reson Med 2007; 58(3):622-630.
24. Morrell G R. A phase-sensitive method of flip angle mapping. Magn Reson Med 2008; 60(4):889-894.
25. Bloch F, Siegert A. Magnetic resonance for nonrotating fields. Phys Rev 1940; 57:522-527.
26. Sacolick L I, Wiesinger F, Hancu I, Vogel M W. B1 mapping by Bloch-Siegert shift. Magn Reson Med 2010; 63(5):1315-1322.
27. Parker G J, Barker G J, Tofts P S. Accurate multislice gradient echo T(1) measurement in the presence of non-ideal RF pulse shape and RF field nonuniformity. Magn Reson Med 2001; 45(5):838-845.
28. Balezeau F, Eliat P A, Cayamo A B, Saint-Jalmes H. Mapping of low flip angles in magnetic resonance. Physics in medicine and biology 2011; 56(20):6635-6647.
29. Voigt T, Nehrke K, Doessel O, Katscher U. T1 corrected B1 mapping using multi-TR gradient echo sequences. Magn Reson Med 2010; 64(3):725-733.
30. Naish J H, Kershaw L E, Buckley D L, Jackson A, Waterton J C, Parker G J M. Modeling of Contrast Agent Kinetics in the Lung Using T-1-Weighted Dynamic Contrast-Enhanced MRI. Magn Reson Med 2009; 61(6): 1507-1514.
31. Parker G J, Roberts C, Macdonald A, Buonaccorsi G A, Cheung S, Buckley D L, Jackson A, Watson Y, Davies K, Jayson G C. Experimentally-derived functional form for a population-averaged high-temporal-resolution arterial input function for dynamic contrast-enhanced MRI. Magn Reson Med 2006; 56(5):993-1000.
32. de Lussanet Q G, van Golde J C, Beets-Tan R G, Post M J, Huijberts M S, Schaper N C, Kessels A G, van Engelshoven J M, Backes W H. Dynamic contrast-enhanced MRI of muscle perfusion combined with MR angiography of collateral artery growth in a femoral artery ligation model. NMR Biomed 2007; 20(8):717-725.
33. Buckley D L, Kershaw L E, Stanisz G J. Cellular-interstitial water exchange and its effect on the determination of contrast agent concentration in vivo: dynamic contrast-enhanced MRI of human internal obturator muscle. Magn Reson Med 2008; 60(5):1011-1019.
34. Zhang J, Amarosa A, Rosenkrantz A B, Kim S. Estimation of reference tissue based arterial input function using neural network. In: Proceedings of the 20th scientific meeting, International Society for Magnetic Resonance in Medicine; 2012; Melbourne.
35. Buckley D L. Uncertainty in the analysis of tracer kinetics using dynamic contrast-enhanced T1-weighted MRI. Magn Reson Med 2002; 47(3):601-606.
36. Nelder J A, Mead R. A Simplex-Method for Function Minimization. Comput J 1965; 7(4):308-313.
37. Kovar D A, Lewis M, Karczmar G S. A new method for imaging perfusion and contrast extraction fraction: input functions derived from reference tissues. J Magn Reson Imaging 1998; 8(5):1126-1134.
38. Sled J G, Pike G B. Correction for B(1) and B(0) variations in quantitative T(2) measurements using MRI. Magn Reson Med 2000; 43(4):589-593.
39. Samson R S, Wheeler-Kingshott C A, Symms M R, Tozer D J, Tofts P S. A simple correction for B1 field errors in magnetization transfer ratio measurements. Magn Reson Imaging 2006; 24(3):255-263.
40. Wang J, Qiu M, Yang Q X, Smith M B, Constable R T. Measurement and correction of transmitter and receiver induced nonuniformities in vivo. Magn Reson Med 2005; 53(2):408-417.
41. Cunningham C H, Pauly J M, Nayak K S. Saturated double-angle method for rapid B1+ mapping. Magn Reson Med 2006; 55(6):1326-1333.
42. Wang D, Zuehlsdorff S, Larson A C. Rapid 3D radiofrequency field mapping using catalyzed double-angle method. NMR Biomed 2009; 22(8):882-890.
43. Deoni S C. Correction of main and transmit magnetic field (B0 and B1) inhomogeneity effects in multicomponent-driven equilibrium single-pulse observation of T1 and T2. Magn Reson Med 2011; 65(4):1021-1035.
44. Ma D, Gulani V, Seiberlich N, Liu K, Sunshine J L, Duerk J L, Griswold M A. Magnetic resonance fingerprinting. Nature 2013; 495(7440):187-192.
45. Jemal A, Siegel R, Ward E, Hao Y, Xu J, Thun M J. Cancer statistics, 2009. CA Cancer J Clin 2009; 59(4): 225-249.
46. Samei E, Saunders R S, Jr., Baker J A, Delong D M. Digital mammography: effects of reduced radiation dose on diagnostic performance. Radiology 2007; 243(2):396-404.
47. Ries L A G, Eisener M P. Cancer of the Female Breast. In: Ries L A G, Young J L, Keel G E, Eiser M P, Lin Y D, Horner M-J, editors. SEER Survival Monograph: Cancer Survival Among Adults: US SEER Program, 1988-2001, Patient and Tumor Characteristics. Volume NIH Pub. No. 07-6215. Bethesda: National Cancer Institute, SEER Program; 2007. p 101-110.
48. Warner E, Messersmith H, Causer P, Eisen A, Shumak R, Plewes D. Systematic review: using magnetic resonance imaging to screen women at high risk for breast cancer Ann Intern Med 2008; 148(9):671-679.
49. Zhang J, Kim S. Uncertainty in MR tracer kinetic parameters and water exchange rates estimated from T-weighted dynamic contrast enhanced MRI. Magn Reson Med 2013.

What is claimed is:

1. A non-transitory computer-accessible medium having stored thereon computer-executable instructions for determining at least one characteristic of at least one tissue, wherein, when a computer arrangement executes the instructions, the computer arrangement is configured to perform procedures comprising:
generating magnetic resonance imaging (MRI) information by encoding at least one portion of at least one time-intensity curve associated with the at least one tissue, which is based on at least one contrast agent concentration, with (i) at least one magnetic resonance (MR) relaxation property of the at least one tissue and (ii) at least one MR measurement condition, by varying at least one MRI scan parameter; and
determining the at least one tissue characteristic based on the MRI information, wherein:
(i) the at least one tissue characteristic includes at least one tissue vascular micro-environmental property,
(ii) the at least one MR measurement condition includes at least one flip angle correction factor, and
(iii) the at least one MRI scan parameter includes at least one of a flip angle or a repetition time (TR).

2. The computer-accessible medium of claim 1, wherein the at least one MR relaxation property includes at least one of at least one T1 value, at least one T2 value or at least one pre-contrast injection T1 value.

3. The computer-accessible medium of claim 1, wherein the at least one MR relaxation property includes at least one factor that estimates a proton density of the at least one tissue.

4. The computer-accessible medium of claim 1, wherein the computer arrangement is further configured to determine the at least one flip angle correction factor based on at least one of a radio frequency (RF) transmit field B1 inhomogeneity, a RF pulse profile, a nonlinearity of a RF amplifier, properties of the at least one tissue or imperfect spoiling in steady-state imaging.

5. The computer-accessible medium of claim 1, wherein the computer arrangement is further configured to scale the at least one flip angle based on the at least one flip angle correction factor.

6. The computer-accessible medium of claim 1, wherein the computer arrangement is further configured to vary the at least one MRI scan parameter before, during, and after an application of at least one contrast injection.

7. The computer-accessible medium of claim 1, wherein the computer arrangement is further configured to determine the at least one tissue characteristic using a parameter estimation procedure based on a constraint that at least one continuous time contrast agent concentration curve of the at least one contrast agent concentration is continuous.

8. The computer-accessible medium of claim 7, wherein the at least one continuous time contrast agent concentration curve is based on the at least one time intensity curve.

9. The computer-accessible medium of claim 1, wherein the MRI information includes at least one dynamic contrast-enhanced (DCE) curve.

10. The computer-accessible medium of claim 9, wherein the dynamic contrast-enhanced DCE MRI curve includes a slow-varying, wash-out portion, of the DCE MRI curve.

11. The computer-accessible medium of claim 1, wherein the computer arrangement is further configured to: (i) approximate a washout portion of the at least one time-intensity curve as at least one line, and (ii) determine the at least one tissue characteristic based on the approximated at least one line.

12. The computer-accessible medium of claim 11, wherein the approximated at least one (i) the at least one line, (ii) a set of line segments, or (iii) contrast kinetic model, connects a beginning and an end of a washout phase having a baseline flip angle and a baseline repetition time.

13. The computer-accessible medium of claim 1, wherein the computer arrangement is further configured to estimate the at least one contrast agent concentration based on a contrast kinetic model of the at least one contrast agent concentration.

14. The computer-accessible medium of claim 13, wherein the contrast kinetic model is a continuous function.

15. The computer-accessible medium of claim 1, wherein the computer arrangement is further configured to generate at least one image of the at least one tissue based on the encoded at least one portion of at least one time-intensity curve.

16. A method for determining at least one characteristic of at least one tissue, comprising:

generating magnetic resonance imaging (MRI) information by encoding at least one portion of at least one time-intensity curve associated with the at least one tissue, which is based on at least one contrast agent concentration, with (i) at least one magnetic resonance (MR) relaxation property of the at least one tissue and (ii) at least one MR measurement condition, by varying at least one MRI scan parameter; and using a computer hardware arrangement, determining the at least one tissue characteristic based on the MRI information, wherein:
(i) the at least one tissue characteristic includes at least one tissue vascular micro-environmental property,
(ii) the at least one MR measurement condition includes at least one flip angle correction factor, and
(iii) the at least one MRI scan parameter includes at least one of a flip angle or a repetition time (TR).

17. A system for determining at least one characteristic of at least one tissue, comprising:
a computer hardware arrangement configured to:
generate magnetic resonance imaging (MRI) information by encoding at least one portion of at least one time-intensity curve associated with the at least one tissue, which is based on at least one contrast agent concentration, with (i) at least one magnetic resonance (MR) relaxation property of the at least one tissue and (ii) at least one MR measurement condition, by varying at least one MRI scan parameter; and determine the at least one tissue characteristic based on the MRI information, wherein:
(i) the at least one tissue characteristic includes at least one tissue vascular micro-environmental property,
(ii) the at least one MR measurement condition includes at least one flip angle correction factor, and
(iii) the at least one MRI scan parameter includes at least one of a flip angle or a repetition time (TR).

* * * * *